(12) United States Patent
Moline et al.

(10) Patent No.: US 11,026,944 B2
(45) Date of Patent: *Jun. 8, 2021

(54) COMPOSITIONS AND METHODS FOR TREATING INSOMNIA

(71) Applicant: Eisai R&D Management Co., Ltd., Tokyo (JP)

(72) Inventors: Margaret Moline, Woodcliff Lake, NJ (US); Gina Pastino, Woodcliff Lake, NJ (US); Yurie Akimoto, Kakamigahara (JP); Yasuhiro Zaima, Kakamigahara (JP); Nobuya Suzuki, Kakamigahara (JP); Nobuo Yoshida, Kakamigahara (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/819,341

(22) Filed: Mar. 16, 2020

(65) Prior Publication Data

US 2020/0268754 A1 Aug. 27, 2020

Related U.S. Application Data

(63) Continuation of application No. 16/255,116, filed on Jan. 23, 2019, now Pat. No. 10,702,529, which is a
(Continued)

(51) Int. Cl.
*A61K 31/506* (2006.01)
*A61K 9/48* (2006.01)
(Continued)

(52) U.S. Cl.
CPC .......... *A61K 31/506* (2013.01); *A61K 9/0053* (2013.01); *A61K 9/2018* (2013.01);
(Continued)

(58) Field of Classification Search
CPC .. A61K 31/506; A61K 9/0053; A61K 9/2018; A61K 9/2054; A61K 9/4858; A61K 9/4866
See application file for complete search history.

(56) References Cited

U.S. PATENT DOCUMENTS 5,935,814 A 8/1999 Bergsma et al.
6,001,963 A 12/1999 Bergsma et al.
(Continued)

FOREIGN PATENT DOCUMENTS

EP 3209298 8/2017
JP 10-229887 9/1998
(Continued)

OTHER PUBLICATIONS

Notice of Allowance in Australian Patent Application No. 2015336463, dated Jun. 26, 2020, 4 pages.
(Continued)

*Primary Examiner* — Savitha M Rao
(74) *Attorney, Agent, or Firm* — Fish & Richardson P.C.

(57) ABSTRACT

In the present invention, compound such as (1R,2S)-2-(((2,4-dimethylpyrimidin-5-yl)oxy)methyl)-2-(3-fluorophenyl)-N-(5-fluoropyridin-2-yl) cyclopropanecarboxamide have been found to be potent orexin receptor antagonists, and may be useful in the treatment of sleep disorders such as insomnia, as well as for other therapeutic uses.

5 Claims, 2 Drawing Sheets

Related U.S. Application Data continuation of application No. 15/519,676, filed as application No. PCT/JP2015/080304 on Oct. 21, 2015, now Pat. No. 10,188,652.

(60) Provisional application No. 62/067,443, filed on Oct. 23, 2014.

(51) Int. Cl.
*A61K 9/00* (2006.01)
*A61K 9/20* (2006.01)

(52) U.S. Cl.
CPC .............. *A61K 9/2054* (2013.01); *A61K 9/48* (2013.01); *A61K 9/4858* (2013.01); *A61K 9/4866* (2013.01)

(56) References Cited

U.S. PATENT DOCUMENTS

| | | | |
|---|---|---|---|
| 6,020,157 | A | 2/2000 | Bergsma et al. |
| 6,166,193 | A | 12/2000 | Yanagisawa |
| 6,309,854 | B1 | 10/2001 | Bergsma et al. |
| 10,188,652 | B2 | 1/2019 | Moline et al. |
| 10,702,529 | B2 | 7/2020 | Moline et al. |
| 2008/0076771 | A1 | 3/2008 | Reiter et al. |
| 2010/0261644 | A1 | 10/2010 | DeFossa et al. |
| 2012/0095031 | A1 | 4/2012 | Terauchi et al. |
| 2012/0165339 | A1 | 6/2012 | Terauchi et al. |
| 2019/0201399 | A1 | 7/2019 | Moline et al. |

FOREIGN PATENT DOCUMENTS

| | | |
|---|---|---|
| JP | 10-327888 | 12/1998 |
| JP | 10-327889 | 12/1998 |
| JP | 11-178588 | 7/1999 |
| JP | 06-328057 | 12/2006 |
| RU | 2458924 | 8/2012 |
| WO | WO 96/034877 | 11/1996 |
| WO | WO 2005/118548 | 12/2005 |
| WO | WO 2007/105177 | 9/2007 |
| WO | WO 2007/129188 | 11/2007 |
| WO | WO 2008/031772 | 3/2008 |
| WO | WO 2008/038251 | 4/2008 |
| WO | WO 2008/069997 | 6/2008 |
| WO | WO 2008/081399 | 7/2008 |
| WO | WO 2009/039942 | 4/2009 |
| WO | WO 2009/047723 | 4/2009 |
| WO | WO 2012/039371 | 3/2012 |
| WO | WO 2016/063995 | 4/2016 |

OTHER PUBLICATIONS

Official Notification in Brazilian Patent Application No. BR112017007063-4, dated Jun. 16, 2020, 4 pages (with English Translation).

Submission Document in Canadian Patent Application No. 2964504, dated Jun. 9, 2020, 10 pages (with English Translation).

[No Author Listed], "2-Part Multiple Ascending Dose Study for Safety and Pharmacokinetics in Healthy and Elderly Subjects", ClinicalTrials.gov, Aug. 28, 2012, E2006-A001-002.

[No Author Listed], "A 2-Part Single Dose Study to Assess the Safety, Tolerability, Pharmacokinetics, and Pharmacodynamics of E2006", ClinicalTrials.gov, Nov. 1, 2011, E2006-A001-001.

[No Author Listed], "A 2-Part Study to Assess Potential Metabolism-Based Drug-Drug Interactions of E2006 When Coadministered With Itraconazole, Rifampin, Midazolam, or Bupropion", ClinicalTrials.gov, Mar. 13, 2014, E2006-A001-004.

[No Author Listed], "A Multicenter, Randomized, Double-blind, Placebo-controlled, Parallel-group, Bayesian Adaptive Randomization Design, Dose Response Study of the Efficacy of E2006 in Adults and Elderly Subjects With Chronic Insomnia", ClinicalTrials.gov, Nov. 27, 2013, E2006-G000-201.

[No Author Listed], "A Study to Determine the Abuse Potential of Single Oral Doses of Lemborexant Compared to Zolpidem, Suvorexant and Placebo in Healthy, Non-Dependent, Recreational Sedative Users", ClinicalTrials.gov, May 17, 2017, E2006-A001-103.

[No Author Listed], "A Study to Determine the Effect of a High-Fat Meal on the Rate and Extent of E2006 Absorption in Healthy Subjects", ClinicalTrials.gov, Mar. 17, 2014, E2006-A001-008.

[No Author Listed], "A Two-Part Study to Evaluate the Safety, Tolerability, Pharmacokinetics, and Pharmacodynamics of E2006 in Healthy Japanese and White Subjects", ClinicalTrials.gov, Jan. 17, 2014, E2006-A001-003.

[No Author Listed], "A Two-Part, Randomized, Double-Blind, Placebo-Controlled, Multiple-Ascending Dose Study to Evaluate the Safety, Tolerability Pharmacokinetics, and Pharmacodynamics of E2006 in Healthy Japanese and White Subjects", Clinical Study Report, Apr. 17, 2015, 12 pages.

[No Author Listed], "An Open-label, Single-dose Study to Determine the Metabolism and Excretion of [14C]E2006 in Healthy Male Subjects", ClinicalTrials.gov, Jan. 27, 2014, E2006-A001-007.

[No Author Listed], "Crossover Study to Evaluate the Effect of Lemborexant Versus Placebo and Zolpidem on Postural Stability, Auditory Awakening Threshold, and Cognitive Performance in Healthy Subjects 55 Years and Older", ClinicalTrials.gov, Jan. 2, 2017, E2006-A001-108.

[No Author Listed], "Long-term Study of Lemborexant in Insomnia Disorder", ClinicalTrials.gov, Nov. 2, 2016, E2006-G000-303.

[No Author Listed], "Open-Label Study of Bioavailability of E2006 Tablet Versus Capsule Formulations", ClinicalTrials.gov, Aug. 28, 2012, E2006-A001-005.

[No Author Listed], "Study of Lemborexant for Irregular Sleep-Wake Rhythm Disorder and Mild to Moderate Alzheimer's Disease Dementia", ClinicalTrials.gov, Dec. 23, 2016, E2006-G000-202.

[No Author Listed], "Study of Lemborexant-Alcohol Interaction in Healthy Subjects", ClinicalTrials.gov, Mar. 30, 2018, E2006-A001-009.

[No Author Listed], "Study of the Efficacy and Safety of Lemborexant in Subjects 55 Years and Older With Insomnia Disorder (Sunrise 1)", ClinicalTrials.gov, May 26, 2016, E2006-G000-304.

[No Author Listed], "Study to Assess the Pharmacokinetic Drug-Drug Interactions of Lemborexant When Coadministered With an Oral Contraceptive, Famotidine, or Fluconazole in Healthy Subjects", ClinicalTrials.gov, Mar. 1, 2018, E2006-A001-012.

[No Author Listed], "Study to Evaluate the Effect of 2 Dosage Strengths of E2006 on a Multiple Sleep Latency Test in Subjects With Insomnia Disorder", ClinicalTrials.gov, Jan. 29, 2015, E2006-A001-107.

[No Author Listed], "Study to Evaluate the Effect of Lemborexant Versus Placebo on Driving Performance in Healthy Adult and Elderly Subjects", ClinicalTrials.gov, Oct. 22, 2015, E2006-E044-106.

[No Author Listed], "Study to Evaluate the Pharmacokinetics of Lemborexant (E2006) and Its Metabolites in Subjects With Mild and Moderate Hepatic Impairment Compared to Healthy Subjects", ClinicalTrials.gov, Feb. 21, 2018, E2006-A001-104.

[No Author Listed], "Study to Evaluate the Pharmacokinetics of Lemborexant and Its Metabolites in Subjects With Normal Renal Function or With Severe Renal Impairment", ClinicalTrials.gov, Feb. 22, 2018, E2006-A001-105.

[No Author Listed], "Study to Evaluate the Respiratory Safety of Lemborexant in Adult and Elderly Healthy Subjects and Adult and Elderly Subjects With Mild Obstructive Sleep Apnea", ClinicalTrials.gov, Mar. 21, 2018, E2006-A001-102.

Bettica et al., "Phase I studies on the safety, tolerability, pharmacokinetics and pharmacodynamics of SB-649868, a novel dual orexin receptor antagonist", Journal of Psychopharmacology, vol. 26, No. 8, GB, Jul. 5, 2011, p. 1058-p. 1070, XP055473159.

Beuckmann, "Development of Lemborexant: A Novel Sleep/Wake Regulator for the Treatment of Insomnia", The 43rd Annual Meeting of Japanese Society of Sleep Research, Jul. 11-13, 2018.

Borgland et al., "Orexin A in the VTA is critical for the induction of synaptic plasticity and behavioral sensitization to cocaine," *Neuron.*, 49:589-601 (2006).

(56) References Cited

OTHER PUBLICATIONS

Brisbare-Roch et al., "Promotion of sleep by targeting the orexin system in rats, dogs and humans " *Nat. Med.*, 13:150-155 (2007).
Chemelli et al., "Narcolepsy in orexin knockout mice: molecular genetics of sleep regulation," *Cell*, 98:437-451 (1999).
Clinical pharmacokinetic studies in pharmacueticals, Jun. 2001, Downloaded from the internet on 018/18/2011) http://www.nihs.go.jp/phar/material/material2/CIPkEng011122.pdf.
Curr Pharm Des. 17(15):1471-75 (2011).
D.A. Prober et al., "26 The Journal of Neuroscience", 2003, p. 13400-p. 13410.
Decision to Grant JP 2012-500752 dated Feb. 28, 2012 (English translation).
Decision to Grant JP 2012-500752 dated Feb. 28, 2012 (in Japanese).
Dorffner et al., "Effect of almorexant treatment on sleep variables in patients with primary insomnia compared with healthy controls," *European Neuropsychopharmacology*, 20(Suppl 3): S252-S253 (2007).
E Mignot et al., "5 Nature Neuroscience Supplement", 2002, p. 1071-p. 1075.
English translation of the allowed claims in JP 2012-500752 dated Feb. 28, 2012.
Equihua et al., "Orexin receptor antagonists as therapeutic agents for insomnia," Frontiers in Pharmacology, 2013, 4(163):1-10.
European Search Report in European Patent Application No. 15851934.8, dated May 18, 2018, 9 pages.
Ida et al., "Possible involvement of orexin the stress reaction in rats," *Biochem. Biophys. Res. Commun.*, 270:318-323 (2000).
International Search Report and Written Opinion for International Patent Application No. PCT/JP2015/080304 dated Jan. 26, 2016.
International Search Report and Written opinion of PCT/JP2011/071325 dated Oct. 18, 2011 (English Translation).
International Search Report and Written opinion of PCT/JP2011/071325 dated Oct. 18, 2011 (in Japanese).
Moline et al., "Dual Orexin Receptor Antagonist Lemborexant (E2006) Shows Efficacy on Sleep Initiation and Maintenance on Sleep Diary Measures in Phase 2 Study," Poster, The 29th Annual Meeting of the Associated Professional Sleep Societies, LLC (APSS), Jun. 6-10, 2015.
Murhpy et al., "Preliminary Efficacy of E2006, a Novel Dual Orexin Receptor Antagonist, for the Treatment of Insomnia Disorder," Poster, Sleep 2014, the 28th Annual Meeting of the Associated Professional Sleep Societies, LLC (APSS); May 31-Jun. 4, 2014.
Murphy et al., "A Phase 1 Study in Healthy Subjects of the Safety and Tolerability of E2006, a Novel Dual Orexin Receptor Antagonist, for the Treatment of Insomnia Disorder," Poster, Sleep 2014, the 28th Annual Meeting of the Associated Professional Sleep Societies, LLC (APSS); May 31-Jun. 4, 2014.
Murphy et al., "Dual Orexin Receptor Antagonist Lemborexant (E2006) Shows Equivalent Efficacy in Men and Women in Phase 2 Study," Poster, Sleep 2015, the annual meeting of the Associated Professional Sleep Societies LLC (APSS), Jun. 10, 2015.
Murphy et al., "Effects of Lemborexant on Sleep Architecture in Subjects with Insomnia Disorder," Poster, Sleep 2016, the 30th annual meeting of the Associated Professional Sleep Societies LLC (APSS), Jun. 11-15, 2016.
Murphy et al., "Lemborexant, A Dual Orexin Receptor Antagonist (DORA) for the Treatment of Insomnia Disorder: Results From a Bayesian, Adaptive, Randomized, Double-Blind, Placebo-Controlled Study", *Journal of Clinical Sleep Medicine*, Nov. 15, 2017 13(11):1289-1299.
National Institute of Health Sciences [online], "Clinical pharmacokinetic studies in pharmaceuticals," Jun. 2001, [Retrieved on 18/18/2011], Retrieved from: URL<http://www.nihs.go.jp/phar/material/material2/CIPkEng011122.pdf>, 23 pages.
Notice of Allowance in Russian Patent Application No. 2017112308, dated Aug. 29, 2019, 17 pages (with English Translation).
Notice of Allowance in Japanese Patent Application No. P2017-522213, dated Jan. 28, 2020, 5 pages (with English Translation).

Office Action in Australian Patent Application No. 2015336463, dated Nov. 22, 2019, 4 pages.
Office Action in Indian Patent Application No. 201747013499, dated Dec. 13, 2019, 6 pages (with English Translation).
Office Action in Israeli Patent Application No. 251759, dated Oct. 17, 2018, 5 pages (with English Translation).
Office Action in Israeli Patent Application No. 251759, dated Aug. 26, 2019, 8 pages (with English Translation).
Office Action in Japanese Patent Application No. P2017-522213, dated Sep. 10, 2019, 7 pages (with English Translation).
Office Action in Mexican Patent Application No. MX/a/2017/004950, dated Aug. 21, 2019, 11 pages (with English Translation).
Office Action in Mexican Patent Application No. MX/a/2017/004950, dated Feb. 18, 2020, 6 pages (with English Translation).
Office Action in Russian Patent Application No. 2017112308, dated May 8, 2019, 11 pages (with English Translation).
Pastino et al., "Lemborexant Does Not Affect the QT interval: high-precision QT analysis from early clinical studies," Poster, 2015 Annual Meeting of the American College of Clinical Pharmacology (ACCP), Sep. 27-29, 2015.
Pastino et al., "Pharmacokinetics of Lemborexant (E2006): Relationship to Efficacy and Safety," Poster, SLEEP 2015, the 29th Annual Meeting of the Associated Professional Sleep Societies, LLC (APSS), Jun. 6-10, 2015.
Pinner et al., "Effects of Lemborexant on Sleep Maintenance in the Latter Half of the Night," Poster, Sleep 2016, the 30th annual meeting of the Associated Professional Sleep Societies LLC (APSS), Jun. 11-15, 2016.
Pinner et al., "Lemborexant Effects on Sleep Maintenance in the Second Half of the Night," Poster, The 2017 Annual Scientific Meeting of the American Geriatrics Society (AGS), May 18-20, 2017.
Request for Expedited Examination of JP 2012-500752 dated Jan. 18, 2012 (English translation).
Request for Expedited Examination of JP 2012-500752 dated Jan. 18, 2012 (in Japanese).
Richey et al., "Pharmacological Advances in the Treatment of Insomnia,".
Sakurai et al., "Orexins and orexin receptors: a family of hypothalamic neuropeptides and G protein-coupled receptors that regulate feeding behavior," *Cell*, 92:573-585 (1998).
Satlin et al., "Dual Orexin Receptor Antagonist E2006 Shows Efficacy on Sleep Initiation and Sleep Maintenance in Phase 2 Study," Poster, ACNP 2014, the 53rd Annual Meeting of the American College of Neuropsychopharmacology, Dec. 7-11, 2014.
Search Results, ClinicalTrials.gov, Aug. 15, 2018.
Shoblock et al., "Selective blockade of the orexin-2 receptor attenuates ethanol self-administration, place preference, and reinstatement," *Psychopharmacology*, 215:191-203 (2011).
Silkis, I.G., "Possible mechanisms of influence of orexin on hippocampus functioning and spatial learning (analytical review)," Journal of Higher Nervous Activity in the name of I.P. Pavlov, 2012, 62(4):389-400 (with partial English translation).
Submission Document in Brazilian Patent Application No. BR112017007063-4, dated Sep. 24, 2018, 16 pages (English Translation).
Submission Document in European Patent Application No. 15851934.8, dated Nov. 26, 2018, 10 pages.
Submission Documentin Israeli Patent Application No. 251759, dated Feb. 11, 2019, 5 pages (English Translation).
Submission Document in Israeli Patent Application No. 251759, dated Dec. 15, 2019, 19 pages (with English Translation).
Submission Document in Mexican Patent Application No. MX/a/2017/004950, dated Oct. 25, 2019, 16 pages (with English Translation).
Submission Document in Russian Patent Application No. 2017112308, dated Jul. 10, 2019, 26 pages (with English Translation).
Submission Document in Singaporean Patent Application No. 11201703064W, dated Apr. 11, 2019, 17 pages.
Vermeeren et al., "Results From an On-Road Driving Performance Study in Non-elderly and Elderly Healthy Subjects With Dual

(56) References Cited

OTHER PUBLICATIONS

Orexin Receptor Antagonist Lemborexant," Poster, Sleep 2018, the 32nd annual meeting of the Associated Professional Sleep Societies LLC (APSS), Jun. 2-6, 2018.
Winrow et al., "Orexin receptor antagonism prevents transcriptional and behavioral plasticity resulting from stimulant exposure," *Neuropharmacology*, 58:185-194 (2010).
Yamadera, "Recent progress in development of hypnotic drugs", Japanese Journal of Clinical Medicine, 1998.02.01, vol. 56, No. 2, p. 245-250 (with partial English translation).
Yeoh et al., "Orexin antagonists for neuropsychiatric disease: progress and potential pitfalls" Frontiers in Neuroscience, 2014, 8(36):1-12.
Submission Document in European Patent Application No. 15851934.8, dated Sep. 18, 2020, 15 pages.
Submission Document in Australian Patent Application No. 2015336463, dated May 15, 2020, 28 pages.
Notice of Allowance in Singaporean Patent Application No. 11201703064W, dated Jul. 16, 2020, 4 pages.
Notice of Allowance in European Patent Applications No. 15851934.8, dated May 27, 2020, 69 pages.
Submission Document in Indian Patent Application No. 201747013499, dated Jun. 5, 2020, 18 pages.
Notice of Allowance in U.S. Appl. No. 16/255,116, dated Jun. 4, 2020, 4 pages.
Notice of Allowance in European Patent Application No. 15851934.8, dated Nov. 5, 2020, 2 pages.
Office Action in Singaporean Patent Application No. 10202007759R, dated Sep. 25, 2020, 7 pages.
Submission Document in Indian Patent Application No. 201747013499, dated Oct. 22, 2020, 4 pages.
Submission Document in Israeli Patent Application No. 251759, dated Nov. 3, 2020, 12 pages (with English Translation).
Office Action in Israeli Patent Application No. 251759, dated Aug. 6, 2020, 6 pages (with English Translation).
Submission Document in Singaporean Patent Application No. 10202007759R, dated Sep. 1, 2020, 6 pages.
Submission Document in Mexican Patent Application No. MX/a/2017/004950, dated Mar. 24, 2020, 13 pages (with English Translation).
Notice of Allowance in Israeli Patent Application No. 251759, dated Nov. 19, 2020, 8 pages (with English Translation).
Submission Document in Brazilian Patent Application No. BR112017007063-4, dated Oct. 13, 2020, 30 pages (with English Translation).
Submission Document in Chinese Patent Application No. 201580055472.X, dated Oct. 9, 2020, 76 pages (with English Translation).
Submission Document in Chinese Patent Application No. 201580055472.X, dated Dec. 15, 2020, 190 pages (with English Translation).
Submission Document in Chinese Patent Application No. 201580055472.X, dated Jan. 6, 2021, 26 pages (with English Translation).
Submission Document in Singaporean Patent Application No. 10202007759R, dated Nov. 27, 2020, 9 pages.
Notice of Allowance in Australian Patent Application No. 2015336463, dated Jun. 5, 2020, 4 pages.
Notice of Allowance in Mexican Patent Application No. MX/a/2017/004950, dated Jul. 23, 2020, 5 pages (with English Translation).
Office Action in Brazilian Patent Application No. BR112017007063-4, dated Jul. 14, 2020, 10 pages (with English Translation).
Office Action in Chinese Patent Application No. 201580055472.X, dated Aug. 7, 2020, 9 pages (with English Translation).
Office Action in Indian Patent Application No. 201747013499, dated Sep. 10, 2020, 3 pages (with English Translation).
Notice of Allowance in Chinese Patent Application No. 201580055472.X, dated Jan. 26, 2021, 8 pages (with English Translation).
Office Action in Chinese Patent Application No. 201580055472.X, dated Mar. 17, 2020, 12 pages (with English Translation).

COMPOSITIONS AND METHODS FOR TREATING INSOMNIA

FIELD OF THE INVENTION

The present invention is directed to compositions and methods for treating insomnia. The present application claims priority on the basis of U.S. Patent Application No. 62/067,443, filed in the United States on Oct. 23, 2014, the contents of which are incorporated herein by reference.

BACKGROUND OF THE INVENTION

Orexin receptors are G-protein coupled receptors found predominately in the brain. Their endogenous ligands, orexin-A and orexin-B, are expressed by neurons localized in the hypothalamus. Orexin-A is a 33 amino acid peptide; orexin-B consists of 28 amino acids (Sakurai T. et al., Cell, 1998, 92 573-585). There are two subtypes of orexin receptors, orexin receptor 1 (hereinafter referred to as OX1) and orexin receptor 2 (hereinafter referred to as OX2); OX1 binds orexin-A preferentially, while OX2 binds both orexin-A and -B. Orexins stimulate food consumption in rats, and it has been suggested that orexin signaling could play a role in a central feedback mechanism for regulating feeding behavior (Sakurai et al., supra). It has also been observed that orexins control wake-sleep conditions (Chemelli R. M. et al., Cell, 1999, 98, 437-451). Orexins may also play roles in brain changes associated with opioid and nicotine dependence (S. L. Borgland et al., Neuron, 2006, 49, 598-601; C. J. Winrow et al., Neuropharmacology, 2010, 58, 185-194), and ethanol dependence (J. R. Shoblock et al., Psychopharmacology, 2011, 215, 191-203). Orexins have additionally been suggested to play a role in some stress reactions (T. Ida et al., Biochem. Biophys. Res. Commun., 2000, 270, 318-323). Compound such as (1R,2S)-2-(((2,4-dimethylpyrimidin-5-yl)oxy)methyl)-2-(3-fluorophenyl)-N-(5-fluoropyridin-2-yl) cyclopropanecarboxamide (hereinafter referred to as Compound A) have been found to be potent orexin receptor antagonists, and may be useful in the treatment of sleep disorders such as insomnia, as well as for other therapeutic uses.

The Formula of Compound A

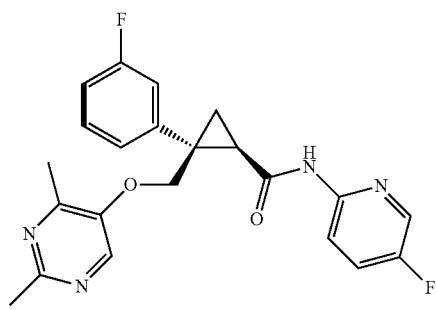

Regarding the hypnotic agent, when an active pharmaceutical ingredient (hereinafter referred to as API) in a pharmaceutical formulation to be taken a once-a-night dosing is too high a dose, it has the potential to cause the next-day residual sleepiness, while the single insufficient dose may cause the patient to wake up during normal sleep period even if the patients are able to fall sleep with the hypnotic. Therefore, it is difficult to set the proper dose with considering the sensitive balance between easy of sleep onset and the avoidance of the residual sleepiness, as compared with the considering only the balance between side effects and efficacy. Furthermore, even if the dose of a certain drug for insomnia, the physiochemical properties of the API and the pharmacokinetic (hereinafter referred to as PK) profile after administration of the drug were known, such information would not be applicable to other APIs for insomnia because it would be likely effected by a number of factors, including the mechanism of action, the route of administration, the rate of absorption, the physiochemical property such as the solubility and the stability in plasma or other factors of each API. Indeed, the relationship between the residual sleepiness and the characteristics of the hypnotic agents is not always consistent (CNS Drugs 2004; 18 (5): 297-328). The relation between PK profile and the sleepiness effect such as the sleep onset or the residual sleepiness has been unknown yet for compound A.

There exists a need in the art for more effective methods of treating insomnia to achieve rapid sleep onset as well as sleep maintenance, throughout the sleep period, but avoid residual sleepiness and/or the next-day impairment, comprising administrating orally a solid dosage form of a hypnotic agent. Further, there exists a need in the art for a pharmaceutical composition comprising a hypnotic agent and at least one pharmaceutically acceptable excipient for the treatment of insomnia to achieve rapid sleep onset as well as sleep maintenance, throughout the sleep period, but avoid residual sleepiness and/or next-day impairment.

SUMMARY OF THE INVENTION

It is an object of the present invention to provide methods of treating insomnia comprising administrating orally a solid dosage form of the drug compound A.

It is further an object of the present invention to provide a pharmaceutical composition, comprising a therapeutically effective amount of compound A In certain embodiments, the present invention to provide methods of treating insomnia, comprises administrating orally a dosage form with a therapeutically effective amount of compound A, wherein said therapeutically effective amount is single daily dose ranging from about 1 mg to about 15 mg.

In certain embodiments, the present invention to provide methods of treating insomnia, comprises administrating orally a dosage form with a therapeutically effective amount of compound A, wherein said therapeutically effective amount is single daily dose ranging from about 2 mg to about 15 mg.

In certain embodiments, the present invention to provide methods of treating insomnia, comprises administrating orally a dosage form with a therapeutically effective amount of compound A, wherein said therapeutically effective amount is single daily dose ranging from about 2 mg to about 10 mg.

In certain embodiments, the present invention to provide methods of treating insomnia, comprises administrating orally a dosage form with a therapeutically effective amount of compound A, wherein said therapeutically effective amount is single daily dose chosen from about 2, 2.5, 4, 5, 8, 10, or 15 mg.

In certain embodiment, the present invention to provide methods of treating insomnia, comprises administrating orally a dosage form with a therapeutically effective amount of compound A, wherein said therapeutically effective amount is single daily dose providing a mean maximum plasma concentration (Cmax) of from about 3.0 ng/ml to about 7.2 ng/ml for each 1 mg of compound A, after single dose administration to human subjects.

In certain embodiment, the present invention to provide methods of treating insomnia, comprises administrating orally a dosage form with a therapeutically effective amount of compound A, wherein said therapeutically effective amount is single daily dose ranging from about 1 mg to about 15 mg, and wherein said single daily dose achieves a mean maximum plasma concentration (Cmax) of from about 3.0 ng/ml to about 7.2 ng/ml for each 1 mg of compound A, after single dose administration to human subjects.

In certain embodiment, the present invention to provide methods of treating insomnia, comprises administrating orally a dosage form with a therapeutically effective amount of compound A, wherein said therapeutically effective amount is single 1 mg daily dose, and wherein said single dose achieves a mean maximum plasma concentration (Cmax) within the range of about 80% to about 125% of 5.3 ng/ml, after single dose administration to human subjects.

In certain embodiment, the present invention to provide methods of treating insomnia, comprises administrating orally a dosage form with a therapeutically effective amount of compound A, wherein said therapeutically effective amount is single 2.5 mg daily dose, and wherein said single daily dose achieves a mean maximum plasma concentration (Cmax) within the range of about 80% to about 125% of 16 ng/ml, after single dose administration to human subjects.

In certain embodiment, the present invention to provide methods of treating insomnia, comprises administrating orally a dosage form with a therapeutically effective amount of compound A, wherein said therapeutically effective amount is single 5 mg daily dose, and wherein said single daily dose achieves a mean maximum plasma concentration (Cmax) of within the range of about 80% to about 125% of 23 ng/ml, after single dose administration to human subjects.

In certain embodiment, the present invention to provide methods of treating insomnia, comprises administrating orally a dosage form with a therapeutically effective amount of compound A, wherein said therapeutically effective amount is single 10 mg daily dose, and wherein said single daily dose achieves a mean maximum plasma concentration (Cmax) within the range of about 80% to about 125% of 36 ng/ml, after single dose administration to human subjects.

In further embodiments, the present invention to provide methods of treating insomnia, comprises administrating orally a dosage form with a therapeutically effective amount of compound A, wherein said therapeutically effective amount is single daily dose to achieve a mean AUC(0-24) of from about 15.9 ng*hr/ml to about 23.8 ng*hr/ml for each 1 mg of compound A, after single dose administration to human subjects.

In further embodiments, the present invention to provide methods of treating insomnia, comprises administrating orally a dosage form with a therapeutically effective amount of compound A, wherein said therapeutically effective amount is single 1 mg daily dose, and wherein said single daily dose achieves a mean AUC(0-24) within the range of about 80% to about 125% of 17 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 2.5 mg daily dose, and wherein said single daily dose achieves a mean AUC(0-24) within the range of about 80% to about 125% of 57 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 5 mg daily dose, and wherein said single daily dose achieves a mean AUC(0-24) within the range of about 80% to about 125% of 95 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 10 mg daily dose, and wherein said single daily dose achieves a mean AUC(0-24) within the range of about 80% to about 125% of 159 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single daily dose to achieve a mean AUC(0-t) of from about 19.1 ng*hr/ml to about 51.1 ng*hr/ml for each 1 mg of compound A, after single dose administration to human subjects.

In further embodiments, the present invention to provide methods of treating insomnia, comprises administrating orally a dosage form with a therapeutically effective amount of compound A, wherein said therapeutically effective amount is single 1 mg daily dose, and wherein said single daily dose achieves a mean AUC(0-t) within the range of about 80% to about 125% of 19 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 2.5 mg daily dose, and wherein said single daily dose achieves a mean AUC(0-t) within the range of about 80% to about 125% of 80 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 5 mg daily dose, and wherein said single daily dose achieves a mean AUC(0-t) within the range of about 80% to about 125% of 128 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 10 mg daily dose, and wherein said single daily dose achieves a mean AUC(0-t) within the range of about 80% to about 125% of 284 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single daily dose to achieve a mean AUC(0-inf) of from about 19.8 ng*hr/ml to about 53.1 ng*hr/ml for each 1 mg of compound A, after single dose administration to human subjects.

In further embodiments, the present invention to provide methods of treating insomnia, comprises administrating orally a dosage form with a therapeutically effective amount of compound A, wherein said therapeutically effective amount is single 1 mg daily dose, and wherein said single daily dose achieves a mean AUC(0-inf) within the range of about 80% to about 125% of 20 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 2.5 mg daily dose, and wherein said single daily dose achieves a mean AUC(0-inf) within the range of about 80% to about 125% of 80 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 5 mg daily dose, and wherein said single daily dose achieves a mean AUC(0-inf) within the range of about 80% to about 125% of 149 ng*hr/ml, after single dose administration to human subjects.

In further embodiments, the present invention to provide methods of treating insomnia, comprises administrating orally a dosage form with a therapeutically effective amount of compound A, wherein said therapeutically effective amount is single 10 mg daily dose, and wherein said single daily dose achieves a mean AUC(0-inf) within the range of about 80% to about 125% of 311 ng*hr/ml, after single dose administration to human subjects.

In certain embodiments, the present invention to provide methods of treating insomnia, comprises administrating orally a dosage form with a therapeutically effective amount of compound A, wherein said therapeutically effective amount is single daily dose ranging from about 1 mg to about 15 mg, and wherein said single daily dose provides a mean plasma compound A concentration of about 20 ng/ml or less at from 8 to 10 hours after single dose administration to human subjects.

In another embodiment, the present invention provides an oral dosage form for treating insomnia comprising a therapeutically effective amount of compound A and at least one pharmaceutically acceptable excipient, wherein said therapeutically effective amount is single daily dose ranging from about 1 mg to about 15 mg.

In another embodiment, the present invention provides an oral dosage form for treating insomnia comprising a therapeutically effective amount of compound A and at least one pharmaceutically acceptable excipient, wherein said therapeutically effective amount is single daily dose to achieve a mean maximum plasma concentration (Cmax) of from about 3.0 ng/ml to about 7.2 ng/ml for each 1 mg of the drug, after single dose administration to human subjects.

In another embodiment, the present invention provides an oral dosage form for treating insomnia comprising a therapeutically effective amount of compound A and at least one pharmaceutically acceptable excipient, wherein said therapeutically effective amount is single 1 mg daily dose, and wherein said single daily dose achieves a mean maximum plasma concentration (Cmax) within the range of about 80% to about 125% of 5.3 ng/ml, after single dose administration to human subjects.

In another embodiment, the present invention provides an oral dosage form for treating insomnia comprising a therapeutically effective amount of compound A and at least one pharmaceutically acceptable excipient, wherein said therapeutically effective amount is single 2.5 mg daily dose, and wherein said single daily dose achieves a mean maximum plasma concentration (Cmax) within the range of about 80% to about 125% of 16 ng/ml, after single dose administration to human subjects.

In another embodiment, the present invention provides an oral dosage form for treating insomnia comprising a therapeutically effective amount of compound A and at least one pharmaceutically acceptable excipient, wherein said therapeutically effective amount is single 5 mg daily dose, and wherein said single daily dose achieves a mean maximum plasma concentration (Cmax) within the range of about 80% to about 125% of 23 ng/ml, after single dose administration to human subjects.

In another embodiment, the present invention provides an oral dosage form for treating insomnia comprising a therapeutically effective amount of compound A and at least one pharmaceutically acceptable excipient, wherein said therapeutically effective amount is single 10 mg daily dose, and wherein said single daily dose achieves a mean maximum plasma concentration (Cmax) within the range of about 80% to about 125% of 36 ng/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single daily dose providing a mean AUC(0-24) of from about 15.9 ng*hr/ml to about 23.8 ng*hr/ml for each 1 mg of the drug, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 1 mg daily dose, and wherein said single daily dose achieves a mean AUC(0-24) within the range of about 80% to about 125% of 17 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 2.5 mg daily dose, and wherein said single daily dose achieves a mean AUC(0-24) within the range of about 80% to about 125% of 57 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 5 mg daily dose, and wherein said single daily dose achieves a mean AUC(0-24) within the range of about 80% to about 125% of 95 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 10 mg daily dose, and wherein said single daily dose achieves a mean AUC(0-24) within the range of about 80% to about 125% of 159 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single daily dose providing a mean AUC(0-t) of from about 19.1 ng*hr/ml to about 51.1 ng*hr/ml for each 1 mg of the drug, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 1 mg daily dose, and wherein said single daily dose achieves a mean AUC(0-t) within the range of about 80% to about 125% of 19 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 2.5 mg daily dose, and wherein said single daily dose achieves a mean AUC(0-t) within the range of about 80% to about 125% of 80 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 5 mg daily dose, and wherein said single daily dose achieves a mean AUC(0-t) within the range of about 80% to about 125% of 128 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 10 mg daily dose, and wherein said single daily dose achieves a mean AUC(0-t) within the range of about 80% to about 125% of 284 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single daily dose providing a mean AUC(0-inf) of from about 19.8 ng*hr/ml to about 53.1 ng*hr/ml for each 1 mg of the drug, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 1 mg daily dose, and wherein said single daily dose achieves a mean AUC(0-inf) within the range of about 80% to about 125% of 20 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 2.5 mg daily dose, and wherein said single daily dose achieves a mean AUC(0-inf) within the range of about 80% to about 125% of 80 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 5 mg daily dose, and wherein said single daily dose achieves a mean AUC(0-inf) within the range of about 80% to about 125% of 149 ng*hr/ml, after single dose administration to human subjects.

In further embodiments, the present invention provides an oral dosage form for treating insomnia comprising a therapeutically effective amount of compound A and at least one pharmaceutically acceptable excipient, wherein said therapeutically effective amount is single 10 mg daily dose, and wherein said single daily dose achieves a mean AUC(0-inf) within the range of about 80% to about 125% of 311 ng*hr/ml, after single dose administration to human subjects.

In certain embodiments, the present invention to provide an oral dosage form for treating insomnia comprising a therapeutically effective amount of compound A and at least one pharmaceutically acceptable excipient, wherein said therapeutically effective amount is single daily dose ranging from about 1 mg to about 15 mg, and wherein said single daily dose provides a mean plasma compound A concentration of about 20 ng/ml or less at from 8 to 10 hours after single dose administration to human subjects.

In certain embodiments, the present invention is directed to an oral pharmaceutical dosage form comprising a pharmaceutically acceptable excipient and an effective amount of compound A for treating insomnia, the dosage form providing an dissolution rate of 85% or more in dissolution medium (0.1 mol/L hydrochloric acid containing 0.5% polysorbate 80, 900 mL, 37±0.5° C.) within 30 minutes from the onset of dissolution study using the Apparatus 2 (Paddle Apparatus, paddle speed; 75 rpm) according to the procedure for immediate-release dosage form in 6.10 Dissolution test of JP16 or <711>Dissolution of USP37.

In certain embodiments, the present invention is directed to an oral pharmaceutical dosage form comprising a pharmaceutically acceptable excipient and an effective amount of compound A for treating insomnia, the dosage form providing an dissolution rate of 85% or more in dissolution medium (0.1 mol/L hydrochloric acid, 900 mL, 37±0.5° C.) within 15 minutes from the onset of dissolution study using the Apparatus 2 (Paddle Apparatus, paddle speed; 50 rpm) according to the procedure for immediate-release dosage form in 6.10 Dissolution test of JP16 or <711>Dissolution of USP37.

In certain embodiments, the present invention is directed to an oral pharmaceutical dosage form comprising lactose as pharmaceutically acceptable excipient.

In certain embodiments, the present invention is directed to an oral pharmaceutical dosage form comprising low-substituted hydroxypropyl cellulose as pharmaceutically acceptable excipient.

In certain embodiments, the present invention is directed to an oral pharmaceutical dosage form comprising lactose and low-substituted hydroxypropyl cellulose as pharmaceutically acceptable excipient.

The method according to the present invention has a potential use of the treatment of insomnia with easy of sleepiness onset, but the avoidance of residual sleepiness and/or the next-day impairment.

The pharmaceutical composition according to the present invention has a potential use of an oral solid dosage for the treatment of insomnia.

Detailed Description

I. DEFINITIONS

In order the invention described herein may be more fully understood, the following definitions are provided for the purposes of the disclosure:

The term "effective amount" means an amount of drug of compound A that is capable of achieving a therapeutic effect in a human subjective in need thereof.

The term "drug of compound A" shall mean (1R, 2S)-2-(((2,4-dimetylpyrimidin-5-yl)oxy) methyl)-2-(3-fluorophenyl)-N-(5-fluoropyridin-2-yl)cyclopropanecarboxamide or a pharmaceutically acceptable salt, hydrate, solvate, polymorph, free-base or any combination thereof.

The term "human subject" shall mean a normal healthy male or female volunteers and/or any individual that presents with clinical signs and symptoms of insomnia or any disease or disorder that causes insomnia.

The term "insomnia" as used herein shall mean all of the description as delineated in the Diagnostic and Statistical Manual of Mental Disorders, 5th Edition (2013) (hereafter referred to as DSM-V), published by the American Psychiatric Association. The DSM-V lists the diagnostic criteria for insomnia as follows:
  A. A predominant complaint is dissatisfaction with sleep quantity or quality, associated with one (or more) of the following symptoms:
     1. Difficulty initiating sleep. (In children, this may manifest as difficulty initiating sleep without caregiver intervention.)
     2. Difficulty maintaining sleep, characterized by frequent awakenings or problems returning to sleep after awakenings. (In children, this may manifest as difficulty returning to sleep without caregiver intervention.)
     3. Early-morning awakening with inability to return to sleep.
  B. The sleep disturbance causes clinically significant distress or impairment in social, occupational, educational, academic, behavioral, or other important areas of functioning.
  C. The sleep difficulty occurs at least 3 nights per week
  D. The sleep difficulty is present for at least 3 months.
  E. The sleep difficulty occurs despite adequate opportunity for sleep.
  F. The insomnia is not better explained by and does not occur exclusively during the course of another sleep-wake disorder (e.g, narcolepsy, breathing-related sleep disorder, circadian rhythm sleep-wake disorder, a parasomnia.).
  G. The insomnia is not attributable to the physiological effects of a substance (e.g., a drug of abuse, a medication).
  H. Coexisting mental disorders and medical conditions do not adequately explain the predominant complaint of insomnia.

Insomnia shall mean a sleep disorder characterized by symptoms including, without limitation, difficulty in falling asleep, difficulty in staying asleep, intermittent wakefulness, and/or waking up too early. The term also encompasses daytime symptoms such as sleepiness, anxiety, impaired concentration, impaired memory, and irritability. Types of insomnia suitable for treatment with the compositions of the present invention include, without limitation, short-term, and chronic insomnia. The term "short-term insomnia" refers to insomnia lasting for about two to about four weeks. The term "chronic insomnia" refers to insomnia lasting for at least one month or longer.

The expression "bioequivalent" or "bioequivalence" is a term of art and is intended to be defined in accordance with Approved Drug Products with Therapeutic Equivalence Evaluations, $34^{th}$ Edition, which is published by the U.S Department of Health and Human Services, and is commonly known as the "Orange Book". Bioequivalence of different formulation of the same drug substance involves equivalence with respect to the rate and extent of drug absorption. The extent and rate of absorption of the test formulation is compared to a reference formulation in order to determine whether the two formulations are bioequivalent. The standard bioequivalence study is conducted in crossover fashion by extensive testing which includes administering single doses of the test and reference drugs to a number of volunteers, usually 12 to 24 healthy normal adults, and then measuring the blood or plasma levels of the drug over time. Detailed guidelines for establishing the bioequivalence of a formulation with a reference formulation have been published by the FDA Office of Generic Drugs, Division of Bioequivalence.

Two formulations whose PK parameters such as Cmax, AUC, or Tmax differ by −20%/+25% or less are generally considered to be "bioequivalent". Another approach for average bioequivalence involves the calculation of a 90% confidence interval for the ratio of the averages (population geometric means) of the measures for the test and reference products. To establish BE, the calculated confidence interval should fall within usually 80-125% for the ratio of the product averages. In addition to this general approach, the others approach, including (1) logarithmic transformation of pharmacokinetic data, (2) methods to evaluate sequence effects and (3) methods to evaluate outlier data, may be useful for the establishment of bioequivalence. For example, in the above (1) the confidence interval should fall within usually 80-125% for the difference in the mean value of the logarithmic converted PK parameter.

The term "sleep time" refers to the time that a subject spends sleeping. Sleep time can be continuous or discontinuous.

"Sleep efficiency" refers to the total sleep time a subject receives during their time in bed. Sleep efficiency is measured by the following equation: 100*(total sleep time (TST)/total time in bed).

The phrase "residual sleepiness" refers to a patient's subjective feeling of sleepiness or sedation upon awakening, usually in the next morning after administration the hypnotic on the evening before. "The next-day impairment" refers to a patient's behavior to impair activities that require alertness, including driving, which occurs when they are awake in the next morning, but levels of the insomnia medicine in their blood remain high enough. The Karolinska sleepiness scale (KSS) is one of a number of tools used for evaluating subjective sleepiness. The KSS was originally developed to constitute a one-dimensional scale of sleepiness and was validated against alpha and theta electroencephalographic (EEG) activity as well as slow eye movement electrooculographic (EOG) activity (Åkerstedt and Gillberg, 1990). Other subjective tests for evaluating residual sleepiness or the next day impairment effect include a Epworth Sleepiness Scale (ESS), a Stanford Sleepiness Scale (SSS), and a Sleep-Wake Activity Inventory (SWAI). Their effects also can be evaluated using one or more of a number of tests to human subjects by those of skill in the art to explore their memory, their attention, information processing and psychomotor performance, including, for example, a Digit Symbol Substitution Test (DSST), a Psychomotor Vigilance Test (PVT), a Choice Reaction Time test (CRT), a Sleep Latency Test (SLT), a Visual Analog Test (VAT), a Symbol Copying Test (SCT), a Critical Flicker Fusion threshold test (CFF), a Simple Reaction time test (visual or auditory; SRT), a Word Learning Test (WLT), a Critical Tracking Test (CTT), a Divided Attention Test (DAT), a digit or letter cancellation test, sleep staging through polysomnographic (PSG) measurements, Continuous Performance Task test (CPT), Multiple Sleep Latency Test (MSLT), a Rapid Visual Information Processing test (RVIP) and others.

The term "dosage form(s)" or "pharmaceutical dosage form(s)" shall mean the means to administer the drug substance (active pharmaceutical ingredient (API)), or to facilitate dosing, administration, and delivery of the medicine to the patient and other mammals. Dosage forms are classified in terms of administration routes and application sites, including, for example, oral, topical, rectal, vaginal, intravenous, subcutaneous, intramuscular, ophthalmic, nasal, otic and inhalation administration. Alternatively, dosage forms are classified in terms of physical form such as solid, semi-solid or liquid. Furthermore, dosage forms are subdivided based on their form, functions and characteristics, including, without limited, tablet, capsule or injection as described in monograph of Japanese Pharmacopoeia 16 edition (JP16) or General Chapter <1151>Pharmaceutical Dosage Forms of U.S. Pharmacopoeia-NF (37)(USP37).

The terms "excipient" shall mean a typically inactive ingredient used as a vehicle (for example, water, capsule shell etc.), a diluent, or a component to constitute a dosage form or pharmaceutical composition comprising a drug such as a therapeutic agent. The term also encompasses a typically inactive ingredient that imparts cohesive function (i.e. binder), disintegrating function (i.e. disintegrator), lubricant function (lubricating agent), and/or the other function (i.e. solvent, surfactant etc.) to the composition.

The term "a mean" refers to a geometric mean. The pharmacokinetic parameters such as "a mean Cmax" or "a mean AUC" refers to the geometric mean value of a Cmax or an AUC.

The list of the abbreviations and definitions of the terms used in this application is presented the following.
AUC: Area under the plasma concentration-time curve
AUC(0-x): Area under the plasma concentration-time curve from time zero to x hours after dosing
AUC(0-t): Area under the plasma concentration-time curve from time zero to time of last quantifiable concentration
AUC(0-inf): Area under the plasma concentration-time curve from time zero to infinity
ANCOVA: Analysis of covariance
CI: Confidence interval
Cmax: Maximum drug concentration
Cx: plasma concentration at x hours after dosing
CV: Coefficient of variation
DSST: Digit Symbol Substitution Test
ECG: Electrocardiogram
EEG: Electroencephalogram
EMG: Electromyogram
EOG: Electrooculogram
KSS: Karolinska Sleepiness Scale
LC-MS/MS: Lipid chromatography-mass spectrometry/mass spectrometry
LPS: Latency to persistent sleep, Duration of time measured from lights off to the first 30 seconds of PSG recording (epoch) of 20 consecutive epochs of non-wake
LS: Least square
MAD: Multiple ascending dose
MTD: Maximum tolerated dose
PD: Pharmacodynamics
PK: Pharmacokinetic(s)
PSG: Polysomnogram, polysomnography
PVT: Psychomotor Vigilance Test
REM: Rapid eye movement
RT: Reaction time
SE: Sleep efficiency, TST divided by the time in bed (min) multiplied by 100
SAD: Single ascending dose
SD: Standard deviation
t1/2: Terminal elimination half-life
tmax: Time to reach maximum (peak) concentration following drug administration
TST: Total sleep time, Duration of rapid eye movement (REM)+non-REM (NREM) sleep during Time in Bed (TIB)
WASO: Wake after sleep onset, Duration of wakefulness from onset of persistent sleep (LPS) to lights-on

II. DESCRIPTION OF THE EMBODIMENTS

Figure 1:
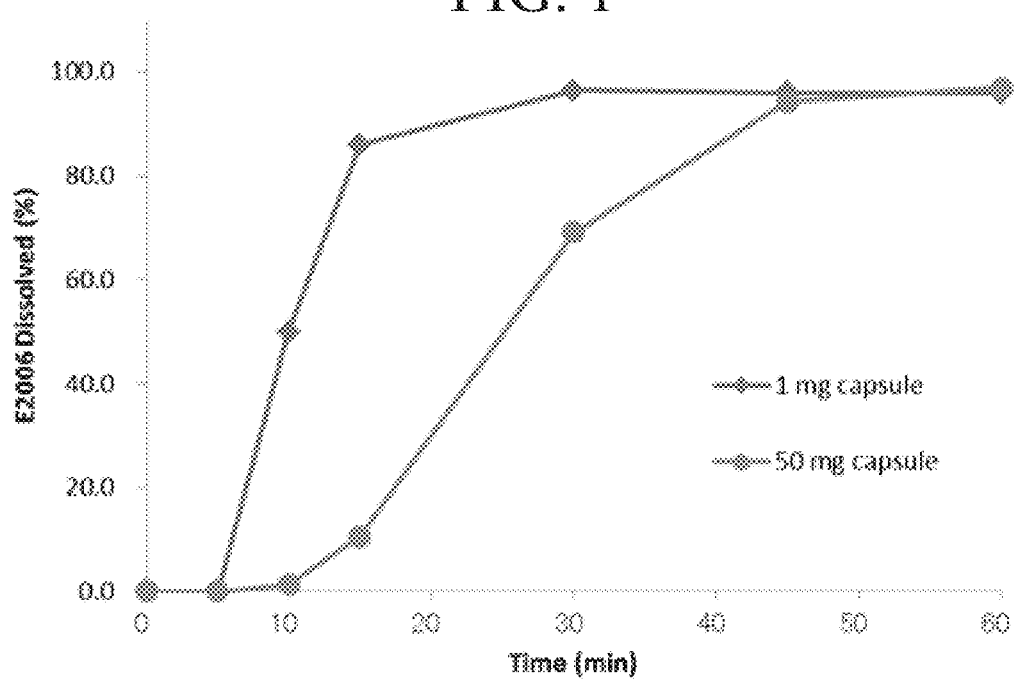
FIG. 1 shows Dissolution Profiles of compound A 1 mg and 50 mg Capsules

In certain embodiments, the present invention is directed to a method of treating insomnia, comprising orally administering a single daily dose of compound A in an amount from about 1 mg to about 15 mg, and wherein said single dose provides easy sleep onset, but avoids residual sleepiness and/or the next-day impairment.

In certain embodiments, the present invention is directed to a method of treating insomnia, comprising orally administering a single daily dose of compound A in an amount from about 1 mg to about 15 mg to achieve a mean maximum plasma concentration (Cmax) of from about 3.0 ng/ml to about 108 ng/ml. Administration of the single daily dose achieves a mean AUC(0-24) of from about 15.9 ng*hr/ml to about 356.4 ng*hr/ml; a mean AUC(0-t) of from about 19.1 ng*hr/ml to about 766.5 ng*hr/ml; a mean AUC(0-inf) of from about 19.8 ng*hr/ml to about 796.5 ng*hr/ml; a mean t1/2 of from about 12.7 to about 60 hours; and a mean time to reach maximum plasma concentration (tmax) from about 1 to about 3.25 hours are achieved.

In another embodiment, the present invention to provide methods of treating insomnia, comprises administrating orally a dosage form with a therapeutically effective amount of compound A, wherein said therapeutically effective amount is single daily dose to achieve a mean maximum plasma concentration (Cmax) of from about 3.0 ng/ml to about 7.2 ng/ml for each 1 mg of compound A. Administration of the single daily dose achieves a mean AUC(0-24) of from about 15.9 ng*hr/ml to about 23.8 ng*hr/ml for each 1 mg of compound A; a mean AUC(0-t) of from about 19.1 ng*hr/ml to about 51.1 ng*hr/ml for each 1 mg of compound A; a mean AUC(0-inf) of from about 19.8 ng*hr/ml to about 53.1 ng*hr/ml for each 1 mg of compound A are achieved.

When a single 1 mg daily dose of compound A is administered to a human subject, a mean maximum plasma concentration (Cmax) of about 5.3 ng/ml; a mean AUC(0-24) of about 17.2 ng*hr/ml; a mean AUC(0-t) of about 19.1 ng*hr/ml; a mean AUC(0-inf) of about 19.8 ng*hr/ml; a mean t1/2 of about 12.7 hours; and a mean time to maximum plasma concentration (tmax) of about 1 hours are achieved.

When a single 2.5 mg daily dose of compound A is administered to a human subject, a mean maximum plasma concentration (Cmax) of from about 10 ng/ml to about 18 ng/ml; a mean AUC(0-24) of about 57 ng*hr/ml to about 60 ng*hr/ml; a mean AUC(0-t) of from about 80 ng*hr/ml to about 95 ng*hr/ml; a mean AUC(0-inf) of from about 80 ng*hr/ml to about 103 ng*hr/ml; a mean t1/2 of from about 30 to about 37 hours; and a mean time to maximum plasma concentration (tmax) of from about 1 to 2 hours are achieved.

When a single 5 mg daily dose of compound A is administered to a human subject, a mean maximum plasma concentration (Cmax) of from about 19 ng/ml to about 23 ng/ml; a mean AUC(0-24) of from about 95 ng*hr/ml to about 110 ng*hr/ml; a mean AUC(0-t) of about 128 ng*hr/ml; a mean AUC(0-inf) of about 150 ng*hr/ml; a mean t1/2 of about 31 hours; and a mean time to maximum plasma concentration (tmax) of from about 1 to about 2 are achieved.

When a single 10 mg daily dose of compound A is administered to a human subject, a mean maximum plasma concentration (Cmax) of from about 30 ng/ml to about 58 ng/ml; a mean AUC(0-24) of from about 160 ng*hr/ml to about 190 ng*hr/ml; a mean AUC(0-t) of from about 280 ng*hr/ml to about 510 ng*hr/ml; a mean AUC(0-inf) of from about 310 ng*hr/ml to about 530 ng*hr/ml; a mean t1/2 of from about 56 to about 60 hours; and a mean time to maximum plasma concentration (tmax) of from about 1 to about 3.25 hours are achieved.

In certain embodiment, when a single 1 mg daily dose of compound A is administered to a human subject, (1) a mean maximum plasma concentration (Cmax) within the range of about 80% to about 125% of 5.3 ng/ml; (2) a mean AUC (0-24) within the range of about 80% to about 125% of 17 ng*hr/ml; (3) a mean AUC(0-t) within the range of about 80% to about 125% of 19 ng*hr/ml; (4) a mean AUC(0-inf) within the range of about 80% to about 125% of 19 ng*hr/ml; and/or (5) a mean time to maximum plasma concentration (tmax) within the range of about 80% to about 125% of 1.0 hour is/are achieved.

In another embodiment, when a single 2.5 mg daily dose of compound A is administered to a human subject, (1) a mean maximum plasma concentration (Cmax) within the range of about 80% to about 125% of 16 ng/ml; (2) a mean AUC(0-24) within the range of about 80% to about 125% of 57 ng*hr/ml; (3) a mean AUC(0-t) within the range of about 80% to about 125% of 80 ng*hr/ml; (4) a mean AUC(0-inf) within the range of about 80% to about 125% of 80 ng*hr/ml; and/or (5) a mean time to maximum plasma concentration (tmax) within the range of about 80% to about 125% of 1.0 hour is/are achieved.

In another embodiment, when a single 5 mg daily dose of compound A is administered to a human subject, (1) a mean maximum plasma concentration (Cmax) within the range of about 80% to about 125% of 23 ng/ml; (2) a mean AUC(0-24) within the range of about 80% to about 125% of 95 ng*hr/ml; (3) a mean AUC(0-t) within the range of about 80% to about 125% of 128 ng*hr/ml; (4) a mean AUC(0-inf) within the range of about 80% to about 125% of 149 ng*hr/ml; and/or (5) a mean time to maximum plasma concentration (tmax) within the range of about 80% to about 125% of 1.6 hours is/are achieved.

In another embodiment, when a single 10 mg daily dose of compound A is administered to a human subject, (1) a mean maximum plasma concentration (Cmax) within the range of about 80% to about 125% of 36 ng/ml; (2) a mean AUC(0-24) within the range of about 80% to about 125% of 159 ng*hr/ml; (3) a mean AUC(0-t) within the range of about 80% to about 125% of 284 ng*hr/ml; (4) a mean AUC(0-inf) within the range of about 80% to about 125% of 311 ng*hr/ml; and/or (5) a mean time to maximum plasma concentration (tmax) within the range of about 80% to about 125% of 1.0 hour is/are achieved.

In certain embodiments, when a single 2.5 mg daily dose is administered over a period of about 14 days, a mean maximum plasma concentration (Cmax) of about 15 ng/ml; a mean AUC(0-24) of about 120 ng*hr/ml; a mean t1/2 of about 44 hours; and a mean time to maximum plasma concentration (tmax) of about 2 hours are achieved.

In certain embodiments, when a single 5 mg daily dose is administered over a period of about 14 days, a mean maximum plasma concentration (Cmax) of about 24 ng/ml; a mean AUC(0-24) of about 190 ng*hr/ml; a mean t1/2 of about 46 hours; and a mean time to maximum plasma concentration (tmax) of about 1 hour are achieved.

In certain embodiments, when a single 10 mg daily dose is administered over a period of about 14 days, a mean maximum plasma concentration (Cmax) of about 47 ng/ml; a mean AUC(0-24) of about 360 ng*hr/ml; a mean t1/2 of about 55 hours; and a mean time to maximum plasma concentration (tmax) of about 2 hours are achieved.

In certain embodiments, the present invention to provide methods of treating insomnia, comprises administrating orally a dosage form with a therapeutically effective amount of compound A, wherein said therapeutically effective amount is single daily dose to provide a mean plasma compound A concentration of about 20 ng/ml or less, at from 8 to 10 hours after single dose administration to human subjects.

In certain embodiments, the present invention to provide methods of treating insomnia, comprises administrating orally a dosage form with a therapeutically effective amount of compound A, wherein said therapeutically effective amount is single daily dose to provide a mean plasma compound A concentration of about 18 ng/ml or less, at from 8 to 10 hours after single dose administration to human subjects.

In certain embodiments, the present invention to provide methods of treating insomnia, comprises administrating orally a dosage form with a therapeutically effective amount of compound A, wherein said therapeutically effective amount is single daily dose to provide a mean plasma compound A concentration of about 15 ng/ml or less, at from 8 to 10 hours after single dose administration to human subjects.

In certain embodiments, the present invention to provide methods of treating insomnia, comprises administrating orally a dosage form with a therapeutically effective amount of compound A, wherein said therapeutically effective amount is single daily dose to provide a mean plasma compound A concentration of about 9.0 ng/ml or less, at from 8 to 10 hours after single dose administration to human subjects.

In certain embodiments, the present invention to provide methods of treating insomnia, comprises administrating orally a dosage form with a therapeutically effective amount of compound A, wherein said therapeutically effective amount is single daily dose to achieve a mean plasma compound A concentration of from about 0.4 ng/ml to about 9.0 ng/ml, at from 8 to 10 hours after single dose administration to human subjects.

In certain embodiments, the present invention to provide methods of treating insomnia, comprises administrating orally a dosage form with a therapeutically effective amount of compound A, wherein said therapeutically effective amount is single daily dose ranging from about 2.5 mg to about 10 mg, and wherein said single daily dose achieves a mean plasma compound A concentration of from about 1.8 ng/ml to about 9.0 ng/ml at 8 hours, or from about 1.5 ng/ml to about 5.0 ng/ml at 9 hours, or from about 2.0 ng/ml to about 8.0 ng/ml at 10 hours, after single dose administration to human subjects.

In certain embodiments, the present invention provides an oral dosage form for treating insomnia, comprising therapeutically effective amount of compound A and at least one pharmaceutically acceptable excipient, wherein said therapeutically effective amount is a single dose ranging from about 1 mg to about 15 mg, and wherein said single dose provides easy sleep onset, but avoids residual sleepiness and/or the next-day impairment.

The dosage form of the present invention achieves: 1) a mean maximum plasma concentration (Cmax) of from about 3.0 ng/ml to about 108 ng/ml; 2) a mean AUC(0-24) of from about 15.9 ng*hr/ml to about 356.4 ng*hr/ml; 3) a mean t1/2 of from about 12.7 to about 60 hours; and 4) a mean time to maximum plasma concentration (tmax) of from about 1 to about 3.25 hours, after single dose administration to a human subjects.

In certain embodiments, the dosage form provides a mean maximum plasma concentration (Cmax) of from about 3.0 ng/ml to about 7.2 ng/ml for each 1 mg of compound A, after single dose administration to human subjects.

In certain embodiments, the dosage form comprises 1 mg of compound A and provides a mean maximum plasma concentration (Cmax) of about 5.3 ng/ml after single dose administration to human subject.

In certain embodiments, the dosage form comprises 2.5 mg of compound A and provides a mean maximum plasma concentration (Cmax) of from about 10 ng/ml to about 18 ng/ml after single dose administration to human subject.

In certain embodiments, the dosage form comprises 5 mg of compound A and provides a mean maximum plasma concentration (Cmax) of from about 19 ng/ml to about 23 ng/ml after single dose administration to human subject.

In certain embodiments, the dosage form comprises 10 mg of compound A and provides a mean maximum plasma concentration (Cmax) of from about 30 ng/ml to about 58 ng/ml after single dose administration to human subject.

In certain embodiments, the dosage form provides a mean AUC(0-24) of from about 15.9 ng*hr/ml to about 23.8 ng*hr/ml for each 1 mg of compound A, after single dose administration to human subjects.

In certain embodiments, the dosage form comprises 1 mg of compound A and provides a mean AUC(0-24) of about 17 ng*hr/ml, after single dose administration to human subjects.

In certain embodiments, the dosage form comprises 2.5 mg of compound A and provides a mean AUC(0-24) of about 57 ng*hr/ml to about 60 ng*hr/ml, after single dose administration to human subjects.

In certain embodiments, the dosage form comprises 5 mg of compound A and provides a mean AUC(0-24) of about 95 ng*hr/ml to about 110 ng*hr/ml, after single dose administration to human subjects.

In certain embodiments, the dosage form comprises 10 mg of compound A and provides a mean AUC(0-24) of about 160 ng*hr/ml to about 190 ng*hr/ml, after single dose administration to human subjects.

In further embodiments, the dosage form provides a mean AUC(0-t) of from about 19.1 ng*hr/ml to about 766.5 ng*hr/ml, after single dose administration to human subjects.

In further embodiments, the dosage form comprises from 1 mg to 15 mg of compound A and provides a mean AUC(0-t) of from about 19.1 ng*hr/ml to about 766.5 ng*hr/ml, after single dose administration to human subjects.

In certain embodiments, the dosage form provides a mean AUC(0-t) of from about 19.1 ng*hr/ml to about 51.1 ng*hr/ml for each 1 mg of compound A, after single dose administration to human subjects.

In certain embodiments, the dosage form comprises 1 mg of compound A and provides a mean AUC(0-t) of about 19 ng*hr/ml, after single dose administration to human subjects.

In certain embodiments, the dosage form comprises 2.5 mg of compound A and provides a mean AUC(0-t) of from about 80 ng*hr/ml to about 95 ng*hr/ml, after single dose administration to human subjects.

In certain embodiments, the dosage form comprises 5 mg of compound A and provides a mean AUC(0-t) of about 128 ng*hr/ml, after single dose administration to human subjects.

In certain embodiments, the dosage form comprises 10 mg of compound A and provides a mean AUC(0-t) of from about 280 ng*hr/ml to about 510 ng*hr/ml, after single dose administration to human subjects.

In further embodiments, the dosage form provides a mean AUC(0-inf) of from about 19.8 ng*hr/ml to about 796.5 ng*hr/ml, after single dose administration to human subjects.

In certain embodiments, the dosage form comprises from about 1 mg to about 15 mg of compound A and provides a mean AUC(0-inf) of from about 19.8 ng*hr/ml to about 796.5 ng*hr/ml, after single dose administration to human subjects.

In certain embodiments, the dosage form provides a mean AUC(0-inf) of from about 19.8 ng*hr/ml to about 53.1 ng*hr/ml for each 1 mg of compound A, after single dose administration to human subjects.

In certain embodiments, the dosage form comprises 1 mg of compound A and provides a mean AUC(0-inf) of about 19.8 ng*hr/ml, after single dose administration to human subjects.

In certain embodiments, the dosage form comprises 2.5 mg of compound A and provides a mean AUC(0-inf) of from about 80 ng*hr/ml to about 103 ng*hr/ml, after single dose administration to human subjects.

In certain embodiments, the dosage form comprises 5 mg of compound A and provides a mean AUC(0-inf) of about 150 ng*hr/ml, after single dose administration to human subjects.

In certain embodiments, the dosage form comprises 10 mg of compound A and provides a mean AUC(0-inf) of from about 310 ng*hr/ml to about 530 ng*hr/ml, after single dose administration to human subjects.

In certain embodiments, the dosage form provides a mean plasma compound A concentration of about 20 ng/ml or less, at from 8 to 10 hours after single dose administration to human subjects.

In certain embodiments, the dosage form provides a mean plasma compound A concentration of about 18 ng/ml or less, at from 8 to 10 hours after single dose administration to human subjects.

In certain embodiments, the dosage form provides a mean plasma compound A concentration of about 15 ng/ml or less, at from 8 to 10 hours after single dose administration to human subjects.

In certain embodiments, the dosage form provides a mean plasma compound A concentration of about 9.0 ng/ml or less, at from 8 to 10 hours after single dose administration to human subjects.

In certain embodiments, the dosage form provides a mean plasma compound A concentration of from about 0.4 ng/ml to about 9.0 ng/ml, at from 8 to 10 hours after single dose administration to human subjects.

In further embodiments, the dosage form comprises a therapeutically effective amount of compound A and at least one pharmaceutically acceptable carrier or excipient, wherein said therapeutically effective amount is single daily dose ranging from about 2.5 mg to about 10 mg, and wherein said single dose achieves a mean plasma compound A concentration of from about 1.8 ng/ml to about 9.0 ng/ml at 8 hours, or from about 1.5 ng/ml to about 5.0 ng/ml at 9 hours, or from about 2.0 ng/ml to about 8.0 ng/ml at 10 hours, after single dose administration to human subjects.

In certain embodiments, the dosage form comprises 1 mg of compound A and provides an elimination half-life (t1/2) of about 12.7 hours after single dose administration to human subjects.

In certain embodiments, the dosage form comprises 2.5 mg of compound A and provides an elimination half-life (t1/2) of from about 30 to 37 hours after single dose administration to human subjects.

In certain embodiments, the dosage form comprises 5 mg of compound A and provides an elimination half-life (t1/2) of about 31 hours after single dose administration to human subjects.

In certain embodiments, the dosage form comprises 10 mg of compound A and provides an elimination half-life (t1/2) of from about 56 to 60 hours after single dose administration to human subjects.

In certain embodiments, the dosage form comprises 1 mg of compound A and provides a mean time to maximum plasma concentration (tmax) of about 1 hour after single dose administration to human subjects.

In certain embodiments, the dosage form comprises 2.5 mg of compound A and provides a mean time to maximum plasma concentration (tmax) of from about 1 to about 2 hours after single dose administration to human subjects.

In certain embodiments, the dosage form comprises 5 mg of compound A and provides a mean time to maximum plasma concentration (tmax) of from about 1 to about 2 hours after single dose administration to human subjects.

In certain embodiments, the dosage form comprises 10 mg of compound A and provides a mean time to maximum plasma concentration (tmax) of from about 1 to about 3.25 hours after single dose administration to human subjects.

In certain embodiment, the present invention provides an oral dosage form for treating insomnia comprising a therapeutically effective amount of compound A and at least one pharmaceutically acceptable excipient, wherein said therapeutically effective amount is single 1 mg daily dose, and wherein said single daily dose achieves (1) a mean maximum plasma concentration (Cmax) within the range of about 80% to about 125% of 5.3 ng/ml; (2) a mean AUC (0-24) within the range of about 80% to about 125% of 17 ng*hr/ml; (3) a mean AUC(0-t) within the range of about 80% to about 125% of 19 ng*hr/ml; (4) a mean AUC(0-inf) within the range of about 80% to about 125% of 19 ng*hr/ml; and/or (5) a mean time to maximum plasma concentration (tmax) within the range of about 80% to about 125% of 1.0 hour.

In another embodiment, the present invention provides an oral dosage form for treating insomnia comprising a therapeutically effective amount of compound A and at least one pharmaceutically acceptable excipient, wherein said therapeutically effective amount is single 2.5 mg daily dose, and wherein said single daily dose achieves (1) a mean maximum plasma concentration (Cmax) within the range of about 80% to about 125% of 16 ng/ml; (2) a mean AUC(0-24) within the range of about 80% to about 125% of 57 ng*hr/ml; (3) a mean AUC(0-t) within the range of about 80% to about 125% of 80 ng*hr/ml; (4) a mean AUC(0-inf) within the range of about 80% to about 125% of 80 ng*hr/ml; and/or (5) a mean time to maximum plasma concentration (tmax) within the range of about 80% to about 125% of 1.0 hour.

In another embodiment, the present invention provides an oral dosage form for treating insomnia comprising a therapeutically effective amount of compound A and at least one pharmaceutically acceptable excipient, wherein said therapeutically effective amount is single 5 mg daily dose, and wherein said single daily dose achieves (1) a mean maximum plasma concentration (Cmax) within the range of about 80% to about 125% of 23 ng/ml; (2) a mean AUC(0-24) within the range of about 80% to about 125% of 95 ng*hr/ml; (3) a mean AUC(0-t) within the range of about 80% to about 125% of 128 ng*hr/ml; (4) a mean AUC(0-inf) within the range of about 80% to about 125% of 149 ng*hr/ml; and/or (5) a mean time to maximum plasma concentration (tmax) within the range of about 80% to about 125% of 1.6 hours.

In another embodiment, the present invention provides an oral dosage form for treating insomnia comprising a therapeutically effective amount of compound A and at least one pharmaceutically acceptable excipient, wherein said therapeutically effective amount is single 10 mg daily dose, and wherein said single daily dose achieves (1) a mean maximum plasma concentration (Cmax) within the range of about 80% to about 125% of 36 ng/ml; (2) a mean AUC(0-24) within the range of about 80% to about 125% of 159 ng*hr/ml; (3) a mean AUC(0-t) within the range of about 80% to about 125% of 284 ng*hr/ml; (4) a mean AUC(0-inf) within the range of about 80% to about 125% of 311 ng*hr/ml; and/or (5) a mean time to maximum plasma concentration (tmax) within the range of about 80% to about 125% of 1.0 hour.

In certain embodiments, the present invention is directed to an oral pharmaceutical dosage form comprising a pharmaceutically acceptable excipient and an effective amount of compound A for treating insomnia, wherein the dosage form provides an dissolution rate of 85% or more within 45 minutes from the onset of dissolution study using the Apparatus 2 (Paddle Apparatus) according to the procedure for immediate-release dosage form in 6.10 Dissolution test of JP16 or <711>Dissolution of USP37. The dissolution medium (900 mL, 37±0.5° C.) is chosen from 0.1 mol/L hydrochloric acid or 0.1 mol/L hydrochloric acid containing 0.5% polysorbate 80. The paddle speed is chosen from 50 rpm or 75 rpm.

In certain embodiments, the present invention is directed to an oral pharmaceutical dosage form comprising a pharmaceutically acceptable excipient and an effective amount of compound A for treating insomnia, wherein the dosage form provides an dissolution rate of 85% or more within 30 minutes from the onset of dissolution study using the Apparatus 2 (Paddle Apparatus) according to the procedure for immediate-release dosage form in 6.10 Dissolution test of JP16 or <711>Dissolution of USP37. The dissolution medium (900 mL, 37±0.5° C.) is chosen from 0.1 mol/L hydrochloric acid or 0.1 mol/L hydrochloric acid containing 0.5% polysorbate 80. The paddle speed is chosen from 50 rpm or 75 rpm.

In certain embodiments, the present invention is directed to an oral pharmaceutical dosage form comprising a pharmaceutically acceptable excipient and an effective amount of compound A for treating insomnia, wherein the dosage form provides an dissolution rate of 85% or more within 15 minutes from the onset of dissolution study using the Apparatus 2 (Paddle Apparatus) according to the procedure for immediate-release dosage form in 6.10 Dissolution test of JP16 or <711>Dissolution of USP37. The dissolution medium (900 mL, 37±0.5° C.) is chosen from 0.1 mol/L hydrochloric acid or 0.1 mol/L hydrochloric acid containing 0.5% polysorbate 80. The paddle speed is chosen from 50 rpm or 75 rpm.

In certain embodiments, the present invention is directed to an oral pharmaceutical dosage form comprising a pharmaceutically acceptable excipient and an effective amount of compound A for treating insomnia, wherein the dosage form provides an dissolution rate of 85% or more in dissolution medium (pH1.2, 900 mL, 37-0.5° C.) within 15 minutes from the onset of dissolution study using the Apparatus 2 (Paddle Apparatus, paddle speed; 50 rpm) according to the procedure for immediate-release dosage form in 6.10 Dissolution test of JP 16 or <711>Dissolution of USP37.

In certain embodiments, the present invention is directed to an oral pharmaceutical dosage form comprising lactose as pharmaceutically acceptable excipient.

In certain embodiments, the present invention is directed to an oral pharmaceutical dosage form comprising low-substituted hydroxypropyl cellulose as pharmaceutically acceptable excipient.

In certain embodiments, the present invention is directed to an oral pharmaceutical dosage form comprising lactose and low-substituted hydroxypropyl cellulose as pharmaceutically acceptable excipient.

In the present invention, compound A may be in the form of free base, a pharmaceutically acceptable salt, hydrate, solvate, polymorph or any combination of the foregoing.

Pharmaceutically acceptable salts may include, but are not limited to, inorganic acid salts (for example, a sulfate, a nitrate, a perchlorate, a phosphate, a carbonate, a bicarbonate, a hydrofluoride, a hydrochloride, a hydrobromide, a hydroiodide); organic carboxylates (for example, an acetate, an oxalate, a maleate, a tartrate, a fumarate, a citrate); organic sulfonates (for example, a methanesulfonate, a trifluoromethanesulfonate, an ethanesulfonate, a benzenesulfonate, a toluenesulfonate, a camphorsulfonate); amino acid salts (for example, an aspartate, a glutamate); quaternary amine salts; alkaline metal salts (for example, a sodium salt, a potassium salt); and alkaline-earth metal salts (for example, a magnesium salt, a calcium salt).

Methods of treating insomnia of the present invention contain compound A in a therapeutically effective amount for treatment of insomnia when administered in accordance with the teachings of the present invention. The effective amount is single daily dose, ranging from 0.5 mg to 100 mg, from 1 mg to 15 mg, from 2 mg to 15 mg, or from 2 mg to 10 mg.

Formulations

Dosage forms of the present invention contain compound A in a therapeutically effective amount for treatment of insomnia when administered in accordance with the teachings of the present invention. Unit dose of the effective amount in a dosage form is from 0.5 mg to 100 mg, from 1 mg to 15 mg, from 2 mg to 15 mg, or chosen from 2 mg, 2.5 mg, 4 mg, 5 mg, 8 mg, 10 mg, or 15 mg. Unit dose is not limited by the type of the dosage form or the number of dosage forms for single dose.

A dosage form in the present invention may constitute one or more pharmaceutical composition comprising compound A together with pharmaceutically acceptable excipients.

The term "composition" used herein includes a product comprising a particular ingredient in a particular amount and any product directly or indirectly brought about by the combination of particular ingredients in particular amounts. Such a term related to the pharmaceutical composition is intended to include a product comprising an active ingredient and an inert ingredient constituting a carrier and include every product directly or indirectly brought about by the combination, complexation or aggregation of any two or more ingredients or the dissociation, other kinds of reactions or interaction of one or more ingredients. Thus, the pharmaceutical composition of the present invention includes every composition prepared by mixing the compound of the present invention with a pharmaceutically acceptable carrier. The term "pharmaceutically acceptable" is used to mean that a carrier, a diluent or a vehicle must be compatible with other ingredients of a preparation and must be nontoxic to a taker.

A dosage form is not limited to as previous said, preferably a solid dosage form; more preferably an oral solid dosage form; furthermore preferably an immediate release oral dosage form.

The dissolution rate of compound A from the dosage form is over 85% within 45 minutes, preferably within 30 minutes, more preferably within 15 minutes, from the onset of dissolution study using the Apparatus 2 (Paddle Apparatus, paddle speed) according to the procedure for immediate-release dosage form in 6.10 Dissolution test of JP16 or <711>Dissolution of USP37. The dissolution medium (900 mL, 37±0.5° C.) is chosen from 0.1 mol/L hydrochloric acid or 0.1 mol/L hydrochloric acid containing 0.5% polysorbate 80. The paddle speed is chose from 50 rpm or 75 rpm.

The term "immediate release" in this invention shall mean a dissolution profile that the dissolution rate of compound A from the dosage form is over 80%, preferably over 85% in dissolution medium (pH1.2, 900 mL, 37±0.5° C.) within 15 minutes from the onset of dissolution study using the Apparatus 2 (Paddle Apparatus, paddle speed; 50 rpm) according to the procedure for immediate-release dosage form in 6.10 Dissolution test of JP16 or <711>Dissolution of USP37.

Solid dosage forms include capsules, granules, lozenges, pellets, pills, powders, suspensions, tablets, preferably capsules, granules, pellets, pills, tablets.

The pharmaceutical composition of the invention may be prepared, using standard techniques and manufacturing processes generally known in the art. See, e.g. the monograph of Japanese Pharmacopoeia 16 edition or General Chapter <1151>Pharmaceutical Dosage Forms of U.S. Pharmacopoeia-NF (37).

The pharmaceutical composition for solid dosage form of the invention may be prepared, for example, powders is prepared by dry blending the components. For example, Compound A, one or more diluents, one or more optional excipients (e.g., binders and/or disintegrants, as well as other additional optional excipients) are blended together. The components of the blend prior to blending, or the blend itself, may be passed through a mesh screen, for example a 400-700 μm mesh screen. A lubricant, which may also be screened, is then added to the blend and blending is continued until a homogeneous mixture is obtained as granules. The mixture is then compressed into tablets. Alternatively, a wet granulation technique can be employed. For example, the active agent and excipient(s) are blended together, for example by using a granulator, and the powder blend is granulated with a small volume of purified water. The resultant wet granule is dried and passed through a mill to obtain as granules. Furthermore, a disintegrator and a lubricant are added to the milled granules and after blending the resultant homogeneous mixture is compressed into tablets. Alternatively, a vehicle such as capsule shells is filled with powders or granules to obtain as capsules. It will be appreciated that modifications of the dry blending and wet granulation techniques, including the order of addition of the components and their screening and blending prior to compression into tablets, may be carried out according to principles well known in the art.

In the case of production of tablets or granules, it may be coated with a water-based film, for example by spray-coating, if necessary.

Examples of diluents used herein include lactose, corn starch and crystalline cellulose etc. Examples of binders used herein include hydroxypropyl cellulose, hypromellose etc. Examples of disintegrators used herein include low-substituted hydroxypropyl cellulose, calcium carboxymethyl cellulose, sodium croscarmellose etc. Examples of lubricants used herein include magnesium stearate, calcium stearate etc. Examples of coloring agents used herein include titanium oxide etc. Examples of coating agents used herein include hydroxypropyl cellulose, hypromellose, methyl cellulose etc. However, needless to say, examples of above agents are not limited thereto.

Detailed Description of the Preferred Embodiments

EXAMPLES

The following examples illustrate various aspects of the present invention. They are not to be construed to limit the claims in any manner whatsoever.

Example 1

Single Dose Study (001 Study)

This was a randomized, double-blind, placebo- and active-controlled, sequential, single-dose study. The study consisted of two parts, Part A (healthy subjects) and Part B (otherwise healthy subjects with primary insomnia).

The primary objective in this study was to evaluate the safety and tolerability of single oral doses of compound A administered in the morning to healthy subjects, and to evaluate selected pharmacodynamic (PD) parameters (e.g., polysomnographically defined sleep measures) with regard to dose response in subjects with primary insomnia following single oral dosing of compound A in the evening approximately 30 minutes prior to the sleep period, compared with 10 mg zolpidem and placebo.

The secondary objective was to evaluate the safety and tolerability of single oral doses of compound A in otherwise healthy subjects with primary insomnia, and to assess the pharmacokinetics (PK) of compound A following administration of single oral doses in healthy subjects and subjects with primary insomnia.

Both parts of the study had two phases, the Prerandomization Phase and the Randomization Phase. The Prerandomization Phase lasted up to 21 days and consisted of a screening period (Day-21 to Day-3) and a baseline period (Day-2 to Day-1) during which each subject's study eligibility was determined and baseline assessments were conducted on Day-2. In the Randomization Phase, subjects were randomized to receive a single oral dose of either compound A or compound A matching placebo (Part A), and/or zolpidem, or zolpidem-matched placebo (Part B).

It was planned to screen approximately 160 healthy subjects and 250 otherwise healthy subjects with primary insomnia in order to enroll 64 and 60 subjects specifically for Part A and Part B, respectively. 160 healthy subjects and 281 otherwise healthy subjects with primary insomnia were actually screened to enroll 64 and 58 subjects into Parts A and B, respectively.

For Part A, 64 healthy subjects were enrolled into cohorts sequentially in a gradual dose escalation manner, to receive either compound A or placebo, and stratified by gender. Each cohort comprised six compound A- and two placebo-treated subjects. All study drugs were administered as single doses using one or more compound A-capsules or compound A-matched placebo capsules due to the test dose. After screening, subjects underwent baseline procedures and randomization on Day-2. Subjects were dosed on Day 1 in the morning after an overnight fast, 1 hour after lights-on. PK blood samples were collected at prespecified timepoints, and PD assessments were performed. Subjects were administered assessments on Day 1 predose and every 2 hours from 2 to 12 hours postdose, and each morning on Days 2 to 6.

These assessments included the Karolinska Sleepiness Scale (KSS), Digit Symbol Substitution Test (DSST), and Psychomotor Vigilance Test (PVT) in order to assess daytime sleepiness, level of alertness, and ability to concentrate. Waketime Questionnaires were administered after PD assessments each morning on Days 1 to Day 6. Time and duration of naps was recorded on Days 1 and 2. Safety was monitored throughout the study.

Doses for Part A were 1 mg, 2.5 mg, 5 mg, 10 mg, 25 mg, 50 mg, 100 mg, and 200 mg of compound A. Escalation to the next higher dose level did not occur until: 1) the safety, tolerability (including laboratory and electrocardiogram [ECG]), and available PK data from the latest completed cohort were reviewed in a blinded manner and 2) the available data supported the increase to the next dose.

For Part B, 58 otherwise healthy subjects with primary insomnia were randomized across three cohorts, and stratified by gender. Part B also included an active control (zolpidem) and matching placebo. In each cohort, there were approximately 12 subjects in the compound A/zolpidem-matched placebo group, approximately four subjects in the zolpidem/compound A-matched placebo group, and approximately four subjects in the compound A-matched placebo/zolpidem-matched placebo group. Part B dosing occurred in the evening, 30 minutes prior to the sleep period. The starting dose for Part B was 3 dose levels that determined to be safe and well tolerated in Part A. Subsequent dose levels in Part B were determined based on the PD results of the first cohort in Part B and PD and safety results from at least 3 completed higher dose cohorts in Part A. Each cohort in Part B was divided into at least two groups, with dosing of each group staggered by a minimum of 2 days.

After the initial Screening visit, eligible subjects were scheduled to return to the clinic for 2 days during the Screening Period to conduct screening/baseline PSGs. These two days occurred at least 3 days after the initial Screening visit and within a window from Day-7 to Day-6 (±2 days). The first PSG was used to screen for sleep apnea and periodic limb movements in sleep (PLMS) and serve as the first baseline PSG. The second PSG was used as the second baseline PSG. Specific PSG variables were used to determine whether subjects met PSG inclusion criteria, and the average of PSG variables from these two PSGs was used as Baseline for this PD measure. Subjects who had met PSG inclusion criteria returned to the clinic on Day-1 for additional baseline procedures and randomization. Subjects were not allowed to nap on Day 1. On the evening of Day 1, after fasting a minimum of 3 hours, study drug was administered 30 minutes prior to the subject's habitual bedtime (lights-out), as calculated from the sleep diary for the first PSG during the Screening Period. PK blood samples were collected at prespecified timepoints, and PD assessments were performed. PSG was recorded on Day 1, postdose. Subjects were administered additional PD assessments each morning on Day 1 through Day 6. These assessments included the KSS, DSST, and PVT, in order to assess daytime sleepiness, level of alertness, and ability to concentrate. The KSS and DSST were also administered 5 minutes predose and 25 minutes postdose on Day 1, just prior to lights-out. Waketime Questionnaires were administered after the PD assessments within 15 minutes of lights-on, on Day 1 to Day 6. Time and duration of naps was recorded on Day 2.

Pharmacokinetic:

For subjects in Part A, Blood samples for determination of plasma concentrations of compound A were collected on Day 1 predose and at 0.25 (15 minutes), 0.5 (30 minutes), 1, 2, 3, 4, 5, 6, 9, 12, 24, 48, 72, 96, 120, 168, and 240 hours after oral administration of compound A, but collected up to 72 hours in the first three cohorts (1, 2.5 and 5 mg compound A groups). PK samples were collected preferentially via an indwelling venous catheter for the first 12 hours and by direct venipuncture thereafter.

For subjects in Part B, blood samples for measurements of plasma concentrations of compound A were obtained by direct venipuncture on Day 1 predose and at 0.5, 9, 12, 24, 36, 60, 84, 108, 156, and 228 hours postdose.

The noncompartmental plasma PK parameters that were calculated for compound A (as data permitted) included, but were not limited to: Cmax (maximum drug concentration); tmax (time to reach maximum (peak) concentration following drug administration); AUC(0-24 h) (area under the concentration x time curve from time zero to time 24 hours); AUC(0-t) (area under the concentration x time curve from time zero to time of last measurable concentration); AUC (0-inf) (area under the concentration x time curve from time zero to infinity); t1/2 (terminal elimination half-life); CL/F (apparent total body clearance of the drug from after extravascular administration); and V/F (apparent volume of distribution).

Plasma concentrations of compound A were measured using a validated liquid chromatography-mass spectrometry/mass spectrometry (LC-MS/MS) assay.

PK parameters of compound A for subjects in Part A were summarized in Table 1. In Part B, the concentration-time profiles were approximately similar to their corresponding dose groups in Part A.

TABLE 1

PK parameters of compound A for subjects in Part A

| | | 1 mg | 2.5 mg | 5 mg | 10 mg | 25 mg | 50 mg | 100 mg | 200 mg |
|---|---|---|---|---|---|---|---|---|---|
| AUC(0-24) | N | 6 | 6 | 6 | 6 | 6 | 6 | 6 | 6 |
| (ng*h/mL) | Mean(SD) | 17.2(3.06) | 56.8(21.1) | 94.6(18.8) | 159(61.9) | 654(97.6) | 1110(321) | 1930(588) | 4080(1040) |
| Cmax | N | 6 | 6 | 6 | 6 | 6 | 6 | 6 | 6 |
| (ng/mL) | Mean(SD) | 5.29(1.25) | 15.9(5.73) | 22.7(4.39) | 36.0(18.7) | 108(22.0) | 168(48.7) | 264(128) | 431(51.1) |
| AUC(0-t) | N | 6 | 6 | 6 | 6 | 6 | 6 | 6 | 6 |
| (ng*h/mL) | Mean(SD) | 19.1(6.18) | 80.2(32.2) | 128(26.5) | 284(80.7) | 1450(455) | 2080(775) | 4490(1300) | 9840(3510) |
| AUC(0-inf) | N | 5 | 4 | 5 | 6 | 6 | 6 | 6 | 6 |
| (ng*h/mL) | Mean(SD) | 19.8(4.01) | 79.7(42.0) | 149(34.3) | 311(90.1) | 1540(518) | 2150(834) | 4740(1420) | 10500(3690) |
| tmax(h) | N | 6 | 6 | 6 | 6 | 6 | 6 | 6 | 6 |
| | Median | 1.00 | 1.01 | 1.55 | 1.00 | 2.01 | 2.53 | 3.00 | 3.00 |
| t1/2 (h) | N | 6 | 6 | 6 | 6 | 6 | 6 | 6 | 6 |
| | Median | 12.70 | 30.10 | 31.35 | 56.15 | 65.50 | 51.85 | 59.75 | 65.20 |
| C9 (ng/mL) | N | 6 | 6 | 6 | 6 | 6 | 6 | 6 | 6 |
| | Mean(SD) | 0.384(0.0726) | 1.54(0.711) | 2.68(0.942) | 4.60(1.39) | 21.9(4.19) | 39.3(14.6) | 86.0(47.5) | 199(119) |

Pharmacodynamic:

Part A Subjects were administered the KSS, DSST, and PVT starting 30 minutes predose on Day 1, then every 2 hours for 12 hours postdose and on Days 2 to 6 starting 30 minutes after lights-on. Waketime Questionnaires were administered on the mornings of Days 1 to 6 following the PD assessments.

In Part A, measures of sleepiness (KSS, DSST, PVT) indicated a general dose-response relationship. Pharmacodynamic response on these measures was generally maximal at 2 hours postdose, coinciding with Cmax. Duration of effect correlated with dose, i.e., the effects were longer with higher doses.

Part B subjects were administered the KSS, DSST, and PVT within 15 minutes after lights-on specifically in that order, on each morning from Day 1 through Day 6, followed by the Waketime Questionnaire. The KSS and DSST were also administered 5 minutes predose and 25 minutes postdose on Day 1 (just prior to lights-out).

In addition, PSG was performed during the Screening Period at Days-7 and -6 (±2 days), and postdose on Day 1. An 8-hour diagnostic PSG consisting of electroencephalogram (EEG), electrooculogram (EOG), electromyogram (EMG), ECGs, leg electrodes, and measures of respiratory function (airflow, respiratory effort, and oxygen saturation) were performed starting at the subject's habitual bedtime as determined from the sleep diary for the 3 nights immediately prior to the first PSG on Day-7 (±2 days). PSG variables from this night were used to screen for sleep apnea and PLMS. On Day-6 (±2) and postdose on Day1, standard PSGs (i.e., not including leg electrodes or measures of respiratory function other than oxygen saturation) were performed. Specified PSG variables from these two PSGs conducted during the Screening Period were used to determine whether subjects met PSG inclusion criteria. The average of PSG variables from these two PSGs conducted during the Screening Period were used as baseline PSG values. The key PD parameters such as PSG LPS, TST, SE, and WASO have been obtained from all PSG recordings.

Polysomnography results indicated preliminary efficacy of compound A. At 2.5 and 10 mg doses, LPS was reduced by almost 30 minutes and at 25 mg, LPS was reduced by approximately 45 minutes relative to Baseline. At 2.5- and 10-mg doses, WASO was reduced by approximately 30 minutes and at 25 mg, WASO was reduced by more than 45 minutes relative to Baseline. Relative to zolpidem, the 2.5- and 10-mg doses of compound A showed a similar magnitude of effect on LPS and WASO. Relative to Baseline, SE was improved by 11% for the 2.5-mg dose of compound A, by 13% for the 10-mg dose, and by 18% for the 25-mg dose. This compared to a change from Baseline in SE of 3% for placebo treatment and 13% for zolpidem. After a single dose of 25 mg of compound A, SE was increased to approximately 90%. However, PD assessments indicated that some individuals at this dose exhibited increases from baseline on measures of next-day residual sleepiness.

There were no clinically significant next day effects of any dose of compound A, zolpidem, or placebo on KSS, DSST, or PVT.

Example 2

Multiple Ascending Dose Study (002 Study)

This was a single-center, randomized, double-blind, placebo-controlled, sequential, multiple-dose study.

Primary objective of this study was to evaluate the safety, tolerability, and pharmacokinetics (PK) of compound A after multiple doses administered orally, once daily in the evening for 14 days in healthy adult subjects. In addition, the objective of this study is to identify the maximum tolerated dose (MTD) or a sufficiently high tolerated dose of compound A to provide a safety margin relative to anticipated therapeutic dose.

A total of 48 healthy adult subjects (18 to 55 years) were to be enrolled into 1 of 6 cohorts sequentially in a gradual dose escalation manner, and randomized to receive either compound A or compound A-matched placebo in the evening 30 minutes before habitual bedtime, and after 3 hours fasting, for 14 days. Each cohort was to comprise 6 compound A-treated subjects and 2 placebo-treated subjects. Blood samples were collected for PK analysis at prespecified timepoints, and PD assessments were conducted.

The study had two phases, the Prerandomization Phase and the Randomization Phase. The Prerandomization Phase lasted up to 21 days and consisted of a screening period (Day-21 to Day-3) and a baseline period (Day-2 to Day-1) during which each subject's study eligibility was determined and baseline assessments were conducted on Day-2. The Randomization Phase (Days 1-28) consisted of 3 periods: Treatment (Days 1-14) during which subjects were randomized and received daily oral doses of either compound A or compound A-matched placebo, Inpatient Follow-up (Days 15-19), and Outpatient Follow-up (Days 20-28) during which PK and safety assessments were conducted.

All subjects were administered PD assessments, including the Karolinska Sleepiness Scale (KSS), Digit Symbol Substitution Test (DSST), and Psychomotor Vigilance Test (PVT) in order to assess acute sleepiness in the interval between dosing and bedtime, as well as next-day residual sleepiness and the level of alertness and ability to concentrate. In addition, a Waketime Questionnaire was administered daily in order to assess quality of sleep on the previous night.

The starting dose for this study was based on the results in the study of Example 1. Escalation to the next higher dose level did not occur until the safety, tolerability (including laboratory and electrocardiogram [ECG]), and available PK data from the latest completed cohort and if the available data supported the increase to the next dose.

Blood samples for determination of plasma concentrations of compound A were collected at Day 1 predose and postdose 0.5 (30 minutes), 1, 1.5, 2, 3, 4, 5, 6, 8, 10, and 12 hours; Days 2 to 13: predose; Day 14: predose and postdose 0.5 (30 minutes), 1, 1.5, 2, 3, 4, 5, 6, 8, 10, and 12 hours; Day 15: 24 hours after Day 14 dose; Days 16 to 19: 36, 60, 84, and 108 hours after Day 14 dose; Day 21, 24, 26, 28: As close as possible to 156, 228, 276, and 324 hours after Day 14 dose. Plasma concentrations of compound A were measured in the same manner as described in Example 1 and the above noncompartmental plasma PK parameters were calculated for compound A.

PD effects were assessed by evaluating postdose and next-day functioning on the KSS, DSST, and the PVT, and by self-report of sleep quality on the Waketime Questionnaire. The KSS, DSST, and PVT were performed starting Day-1 at 15 minutes before habitual bedtime; on Days 1 to 15 within 15 minutes after habitual waketime, and at 1, 2, 4, 8, and 12 hours after habitual waketime, and on Days 1 to 14 at 15 minutes predose and 15 minutes postdose. 24-hour Holter recordings were started 30 minutes before bedtime on Day-2 and just prior to dosing on Day 14. Extractions from these recordings were used to conduct ECG analyses, including the HPQT analysis. Waketime Questionnaires were administered on Day 1 to Day 19.

The KSS, PVT, and DSST were administered on each treatment day in the evening predose and postdose to assess the acute effect of compound A on sleepiness. For these timepoints, the daily 15 minutes predose values on the KSS, DSST, and PVT served as a baseline for that day's 15 minutes postdose value (daily baseline). The KSS, PVT, and DSST were also administered throughout the daytime hours subsequent to each dosing evening to assess the effect of compound A on next-day residual sleepiness. For these timepoints, the assessments taken at Day 1, 15 minutes and 1, 2, 4, 8, and 12 hours after habitual waketime served as the baseline for the assessments taken at the corresponding times after habitual waketime on Day 2 to Day 15 (time-matched baseline). Waketime Questionnaires were administered on Day 1 through Day 19 in the morning hours. The predose value on Day 1 was used as the baseline. The difference between placebo and each dose of compound A in change from baseline at each timepoint was calculated along with 95% confidence intervals (CIs). Potential dose-response and time trend were explored as data allowed.

Compound A capsules and compound A-matched placebo capsules were available in strengths of 2.5 mg, 10 mg, and 50 mg. All study drugs were administered as daily doses using one or more compound A-capsules or compound A-matched placebo capsules due to the test dose.

Pharmacokinetic

PK parameters on Day1 and Day 14 were summarized in Table 2 and Table 3 respectively.

TABLE 2

PK parameters on Day 1

|  |  | 2.5 mg | 5 mg | 10 mg | 25 mg | 50 mg | 75 mg |
|---|---|---|---|---|---|---|---|
| AUC(0-24) (ng*h/mL) | N | 6 | 6 | 6 | 6 | 5 | 6 |
|  | Mean(SD) | 59.4(17.5) | 108(34.9) | 187(47.9) | 549(104) | 931(253) | 1260(301) |
| Cmax (ng/mL) | N | 6 | 6 | 6 | 6 | 5 | 6 |
|  | Mean(SD) | 10.1(4.26) | 19.4(7.91) | 30.4(13.1) | 92.0(24.0) | 199(81.2) | 223(103) |
| tmax (h) | N | 6 | 6 | 6 | 6 | 5 | 6 |
|  | Median | 2.015 | 1.250 | 3.250 | 1.500 | 2.000 | 3.000 |
| C8 (ng/mL) | N | 6 | 6 | 6 | 6 | 5 | 6 |
|  | Mean(SD) | 2.33(0.967) | 4.40(1.73) | 8.51(2.89) | 24.1(9.26) | 38.1(11.0) | 54.5(21.7) |
| C10 (ng/mL) | N | 6 | 6 | 6 | 6 | 5 | 6 |
|  | Mean(SD) | 2.04(0.769) | 3.63(1.23) | 7.72(4.13) | 19.8(7.11) | 32.9(10.2) | 44.2(13.4) |

TABLE 3

PK parameters on Day14

|  |  | 2.5 mg | 5 mg | 10 mg | 25 mg | 50 mg | 75 mg |
|---|---|---|---|---|---|---|---|
| AUC(0-24) (ng*h/mL) | N | 6 | 6 | 6 | 5 | 5 | 5 |
|  | Mean(SD) | 120(38.0) | 186(87.5) | 357(193) | 1100(387) | 2300(758) | 3790(857) |
| Cmax (ng/mL) | N | 6 | 6 | 6 | 5 | 5 | 5 |
|  | Mean(SD) | 15.4(4.73) | 24.0(10.7) | 46.9(14.5) | 107(38.9) | 220(33.5) | 420(140) |
| tmax (h) | N | 6 | 6 | 6 | 5 | 5 | 5 |
|  | Median | 2.000 | 1.000 | 1.750 | 3.000 | 2.020 | 2.000 |
| t1/2 (h) | N | 6 | 6 | 6 | 5 | 5 | 5 |
|  | Mean(SD) | 43.8(13.1) | 45.6(16.6) | 55.0(23.8) | 50.6(10.7) | 55.5(21.3) | 56.2(20.1) |

Based on graphical assessment of dose-normalized data, Cmax increased slightly less than in proportion to dose for both Day 1 and Day 14 assessments. Based on dose-normalized data, AUC(0-24 h) increased slightly less than in proportion to dose on Day 1 but increased in approximate proportion to dose based on Day 14 assessments. The terminal half-life for the 2.5- and 5-mg doses were similar, averaging approximately 45 hours. At doses of 10 mg and higher, the mean terminal half-life was approximately 55 hours following the last day of Day 14 dosing. Accumulation was lower than predicted by the terminal half-life. Based on accumulation, the effective half-life was ranged from 16.9 to 24.7 hours for doses ranging from 2.5 to 25 mg, and 28.0 and 39.3 hours for the 50- and 75-mg doses, respectively.

Pharmacodynamics

Next-day residual sleepiness effect: There were dose-related increases in both the magnitude and duration of next day residual sleepiness as measured by the KSS, PVT, and DSST. In the 2.5-mg and 5-mg dose groups, there was no meaningful difference from placebo indicative of an increase in next-day residual sleepiness groups on any assessment at any time relative to waketime on any treatment day. Slight differences from placebo were observed in the 10-mg dose group at timepoints within 2 hours after waketime on the KSS on Day 2 through Day 4. In the 25-mg dose group, the increase in next-day residual sleepiness was more consistent and slightly larger than in the 10-mg dose group. The effect was again, limited to timepoints within 2 hours after waketime, but was observed on the KSS and to some extent on PVT Lapses and PVT Mean RRT. The differences from placebo were most consistent and larger on Day 2 and Day 15, compared with all other treatment days. In the 50-mg and 75-mg dose groups, there were consistent and relatively large differences from placebo on all assessments of sleepiness. These differences were of greater magnitude at timepoints within 2 hours after waketime, but were still observed at 4 hours and 8 hours after waketime, particularly on the PVT Mean RRT. By 12 hours after waketime, there were no differences from placebo on any measures of sleepiness in any dose group on any day. For dose groups in which next-day residual sleepiness was observed (ie, 10 mg and higher), sleepiness was relatively greater on Days 2 to 4 vs Days 5 to 15. This pattern of lessening sleepiness across treatment days was generally observed, despite accumulation of compound A in plasma.

None of the items on the Waketime Questionnaire indicated a systematic pattern of changes in nighttime sleep in any dose group or the placebo group, with the exception that the Quality of Sleep scale showed a trend for more subjects in both the placebo and compound A groups to report "restless" or "very restless" sleep on Day 2 and especially on Day 15, relative to other days.

Pharmacokinetic-Pharmacodynamics

For the PK-PD exploratory analysis of next-day residual sleepiness, population PK model-derived compound A plasma concentrations at 8, 9, and 10 hours following administration on the evening of Day 1 were related to change from baseline on the KSS, PVT Lapses, and DSST at 15 minutes, 1 hour, and 2 hours after waketime on the morning of Day 2, respectively. At all timepoints, both KSS and the PVT Lapses were observed to increase more from baseline with increasing compound A concentrations. Concentrations below 30 ng/mL (which occur at doses below 25 mg) after 9-10 hours postdose, which correspond to the 1-2 hours after morning awakening, were associated with minimal or no change from baseline on the KSS, PVT Lapses, or DSST.

Example 3

Crossover Study of Relative Bioavailability of Tablet Versus Capsule Formulation (005 Study)

Single-center, open-label, randomized crossover study was conducted to evaluate, in healthy adult subjects, the bioavailability of single solid oral doses of compound A in tablet formulation relative to single oral doses of compound A in capsule formulation at 2.5, 10, and 25 mg. Another objective of the study was to evaluate the safety and tolerability of tablet formulations of compound A at 2.5, 10, and 25 mg in healthy adult subjects. Approximately 36 subjects were randomly assigned to one of three cohorts (approximately 12 subjects per cohort) and received both a single dose of compound A as a capsule formulation and a single dose of compound A as a tablet formulation, in random sequence, in a 1:1 ratio. The doses were 2.5 mg, 10 mg, and 25 mg.

The study had two phases: Prerandomization and Randomization. The Prerandomization Phase lasted for up to 21 days and included a Screening Period and Baseline Period A, during which eligibility was established and baseline assessments before dosing of the first formulation occurred. The Randomization Phase consisted of two Treatment Periods (A and B), separated by Baseline Period B. On the first day of Treatment Period A, subjects received a single oral dose of the first formulation. After the first formulation dose, pharmacokinetic (PK) and safety assessments were obtained throughout Treatment Period A, and subjects completed a 20-day washout. Before dosing of the second formulation, subjects completed Baseline Period B assessments. Subjects then proceeded to Treatment Period B and received a single oral dose of the second formulation. Pharmacokinetic and safety assessments were obtained throughout Treatment Period B.

Plasma concentrations of compound A were measured using a validated liquid chromatography-tandem mass spectrometry (LC-MS/MS) assay.

Noncompartmental methods were used to calculate the following plasma PK parameters for compound A: area under the plasma concentration-time curve from time zero to 8 hours after dosing (AUC(0-8)), area under the plasma concentration-time curve from time zero to 72 hours after dosing (AUC(0-72)), area under the plasma concentration-time curve from time zero to time of the last quantifiable concentration (AUC(0-t)), area under the plasma concentration-time curve from time zero extrapolated to time infinity (AUC(0-inf)), maximum observed plasma drug concentration (Cmax), terminal elimination half-life (t1/2), absorption lag time (tlag), and time to reach the maximum (peak) plasma concentration after drug administration (tmax). The primary PK parameters were AUC(0-inf) and Cmax. The individual PK parameters of compound A were presented in the data listings by formulation (tablet or capsule) and dose (2.5, 10, or 25 mg). The PK parameters except tmax and tlag were summarized by formulation and dose using descriptive statistics: number of subjects, mean, SD, coefficient of variation, geometric mean, median, minimum, and maximum. The parameters tmax and tlag were summarized by formulation and dose using the following descriptive statistics: median, minimum, maximum, and the 90% confidence interval (CI) of the median point estimate. The natural log (ln)-transformed PK parameters for compound A (AUC(0-inf), Cmax, AUC(0-8), AUC(0-72), and AUC(0-t)) were compared separately by dose with a mixed-effects model with sequence, treatment period, and formulation as fixed effects and subjects nested within sequence as a random effect. The ratio of geometric least squares (LS) means (tablet formulation as test/capsule formulation as reference) and corresponding 90% CI were computed by exponentiation of the LS mean difference and corresponding 90% CI.

PK parameters of compound A were summarized in Table 4.

TABLE 4

PK parameters of compound A (Tablet versus Capsule)

|  | 2.5 mg | | 10 mg | | 25 mg | |
| --- | --- | --- | --- | --- | --- | --- |
|  | Tablet | Capsule | Tablet | Capsule | Tablet | Capsule |
| N | 12 | 12 | 12 | 12 | 15 | 13 |
| AUC(0-8) (ng*h/mL) Mean(SD) | 47.1(16.3) | 45.5(14.8) | 178(62.2) | 164(44.3) | 386(67.0) | 358(88.7) |
| AUC(0-72) (ng*h/mL) Mean(SD) | 84.3(30.8) | 85.1(27.4) | 341(135) | 372(114) | 795(199) | 803(234) |
| AUC(0-t) (ng*h/mL) Mean(SD) | 93.2(40.0) | 94.9(34.6) | 455(214) | 511(222) | 1070(350) | 1080(368) |
| AUC(0-inf) (ng*h/mL) Mean(SD) | 101(42.9) | 103(39.3) | 472(222) | 531(234) | 1100(366) | 1110(379) |
| Cmax (ng/mL) Mean(SD) | 18.0(7.50) | 15.9(5.93) | 58.1(24.0) | 49.0(16.5) | 120(26.7) | 105(33.0) |
| tmax (h) (median) | 1.00 | 1.00 | 1.00 | 1.50 | 1.00 | 1.50 |
| t1/2 (h) Mean(SD) | 35.1(14.6) | 36.8(17.2) | 59.5(19.0) | 57.0(22.0) | 57.6(18.7) | 57.4(20.5) |
| C8 (ng/mL) Mean(SD) | 1.75(0.610) | 1.84(0.618) | 7.44(3.23) | 8.90(2.70) | 17.6(6.11) | 19.9(7.62) |

Blood samples for the determination of plasma concentrations of compound A were collected at the following times: Treatment Period A (Day 1 to Day 15): before and after dosing at 0.5 (30 minutes), 1, 1.5, 2, 3, 4, 5, 6, 8, 12, 24, 48, 72, 120, 168, 240, and 336 hours; Treatment Period B (Day 22 to Day 36): before and after dosing at 0.5 (30 minutes), 1, 1.5, 2, 3, 4, 5, 6, 8, 12, 24, 48, 72, 120, 168, 240, and 336 hours.

Differences between formulations (Treatment A [tablet] compared to Treatment B [capsule]) in AUC(0-8), AUC(0-72), AUC(0-t), and AUC(0-inf) across all dose levels were each less than 13%. Differences between the tablet and capsule formulations in Cmax across all dose levels were each less than 16%. The median tmax was observed at 1 to 1.5 hours after administration of both the tablet and capsule formulations across all dose levels. A trend of a 30-minute delay in median tmax for the capsule formulation (Treatment B) compared to the tablet formulation (Treatment A) was observed at higher doses. There was no observed absorption lag in either formulation at any dose level.

Overall, the results indicate that both the rate and extent of compound A absorption after tablet administration are comparable to the reference capsule for all strengths tested. Variability in the derived PK parameters was also similar for the tablet compared to capsule treatments. These results support the conclusion that the relative bioavailability of the tablet at strengths of 2.5, 10, and 25 mg is similar to corresponding strengths of the capsule. Thus, clinical transition to the tablet formulation can be made without dose adjustment relative to the capsule.

Example 4 (201 Study)

This was a multi-center, randomized, double-blind, adaptive design, dose-response study in subjects with insomnia. Subjects were randomized to 1 of 6 doses of compound A (1 mg, 2.5 mg, 5 mg, 10 mg, 15 mg and 25 mg) or placebo.

The primary objectives of the study were to:
1. Identify a dose or doses of compound A that maximize efficacy and minimize next-day residual sleepiness in subjects with chronic insomnia at the beginning of treatment by comparing the effect of 6 doses of compound A with placebo using a composite utility function incorporating change from baseline on sleep efficiency (SE) and change from baseline on the Karolinska Sleepiness Scale (KSS) at 1 hour after morning waketime after dosing on Day 2 and Day 3.
2. Compare the effect of 6 doses of compound A with placebo on the KSS at 1 hour after morning waketime on Day 15 and Day 16 in subjects with chronic insomnia, in order to confirm that the dose or doses that maximize efficacy and minimize next-day residual sleepiness at the beginning of treatment are not associated with treatment unacceptable levels of next-day residual sleepiness at the end of treatment.

The additional objectives of the study were to evaluate:
1. Efficacy at beginning of treatment:
Overall: Compare each dose level of compound A with placebo on change from mean SE at baseline to mean SE after dosing on Day 1 and Day 2
Sleep induction: Compare each dose level of compound A with placebo on change from mean latency to persistent sleep (LPS) at baseline to mean LPS after dosing on Day 1 and Day 2 Sleep maintenance: Compare each dose level of compound A with placebo on change from mean wakefulness after sleep onset (WASO) at baseline to mean WASO after dosing on Day 1 and Day 2
2. Efficacy at end of treatment: Overall: Compare each dose level of compound A with placebo on change from mean SE at baseline to mean SE after dosing on Day 14 and Day 15
Sleep induction: Compare each dose level of compound A with placebo on change from mean LPS at baseline to mean LPS after dosing on Day 14 and Day 15 Sleep maintenance: Compare each dose level of compound A with placebo on change from mean WASO at baseline to mean WASO after dosing on Day 14 and Day 15
3. Potential habituation of efficacy from beginning to end of treatment:
Overall: Compare each dose level of compound A with placebo on change from mean SE at baseline to mean SE after dosing on Day 1 and Day 2 versus change from mean SE at baseline to mean SE after dosing on Day 14 and Day 15
Sleep induction: Compare each dose level of compound A with placebo on change from mean LPS at baseline to mean LPS after dosing on Day 1 and Day 2 versus change from mean LPS at baseline to mean LPS after dosing on Day 14 and Day 15
Sleep maintenance: Compare each dose level of compound A with placebo on change from mean WASO at baseline to mean WASO after dosing on Day 1 and Day 2 versus change from mean WASO at baseline to mean WASO after dosing on Day 14 and Day 15

A total of 616 subjects were screened, and 291 of these subjects were randomized to the study; 56 to placebo, 32 to 1 mg, 27 to 2.5 mg, 38 to 5 mg, 32 to 10 mg, 56 to 15 mg and 50 to 25 mg. 291 subjects were contained in the Full Analysis Set, Safety Analysis Set, and PD Analysis Set. There were 222 subjects in the active dose groups (roughly equal over all doses, 90 to 100%) and 51 (91.1%) in the placebo group who completed the planned treatment regimen.

The study had 2 phases: Prerandomization and Randomization. The Prerandomization Phase lasted up to 21 days and consisted of a Screening Period (Days-21 to -2) and a Baseline Period (Day-1). After the Baseline Period, all eligible subjects were randomized in a double-blind manner to receive compound A or placebo for 15 nights during the Treatment Period (Days 1 to 15). All subjects then received placebo in a single-blind manner, for 2 nights (Days 16 to 17) during the Rebound Insomnia Assessment Period (Days 16 to 18). Subjects did not receive study drug during the Follow-up Period (Days 19 to 30). All subjects came to the clinic for screening procedures. During the Screening Period, subjects completed the Sleep Diary each day. Polysomnographic sleep was measured during the Screening Period on 2 consecutive nights between Day-9 and Day-3. The 8-hour polysomnograms (PSGs) were started at the median habitual bedtime calculated from responses on the Sleep Diary, which were completed for 7 days before the first PSG night. These recordings served as both eligibility screening PSGs and as Baseline PSGs. Subjects could leave the clinic between the screening/Baseline PSG nights.

All subjects returned to the clinic on Day-1 for Baseline Period procedures. They remained in the clinic until Day 3. Morning assessments on Day 1 provided the Baseline values for the KSS, the Digit Symbol Substitution Test (DSST), and the Reaction Time Index (RTI). Assessments at 6 hours after waketime provided the Baseline values for the Waking Function Battery (WFB), and the Profile of Mood States-Brief (POMS-B). Subjects were then randomized to receive 1 of 6 doses of compound A or placebo for the next 15 days. Study drugs were tablets containing compound A-matched placebo or compound A of 1 mg, 2.5 mg, 5 mg, or 10 mg and to be ingested 30 minutes before the median habitual bedtime calculated from their Sleep Diary responses during the Screening Period. An 8-hour PSG, starting at the same bedtime as used for the screening and Baseline PSG nights, was recorded on the first 2 treatment nights (Days 1 and 2). The Sleep Diary continued to be completed each day in the clinic, and assessments of insomnia severity (ISI), next-day residual effects (KSS, DSST, and RTI) were conducted while subjects were in the clinic. On specified study days, plasma concentrations of compound A were assessed while subjects were in the clinic in the morning after awakening and at trough just before dosing.

Subjects continued to take compound A or placebo 30 minutes before their anticipated, self-selected bedtime and continued to complete the Sleep Diary each day while at home during the Treatment Period. On Day 14 of the Treatment Period, subjects returned to the clinic. They remained in the clinic for 4 nights and the intervening days until Day 18. Eight-hour PSGs were recorded each night in the clinic, to start at the median habitual bedtime calculated from responses on the Sleep Diary completed on Days 3 to 13. The Sleep Diary continued to be completed each day in the clinic, and the ISI, KSS, DSST, RTI, were administered at prespecified time points during the daytime hours.

After the Treatment Period ended, all subjects received placebo in a single-blind manner on the final 2 nights spent in the clinic (Days 16 and 17). On these 2 nights, 8-hour PSGs starting on the same bedtime as Days 14 and 15 were recorded to assess for rebound insomnia (Rebound Insomnia Assessment Period).

During the Treatment period, blood samples for plasma concentrations of compound A were obtained within 30 minutes predose each night (except on Day 1) in the clinic and within 1 hour of morning waketime following each night spent in the clinic. Plasma concentrations of compound A were measured using a validated liquid chromatography-tandem mass spectrometry (LC-MS/MS) assay.

The KSS was used to measure next-day residual effects at prespecified timepoints. In this test, subjects rate their sleepiness using the KSS, a 9-point verbally anchored scale. Categories and scores range from "extremely alert" (score=1), "alert" (3), "neither alert nor sleepy" (5), "sleepy-but no difficulty remaining awake" (7), to "extremely sleepy-fighting sleep" (9). The key outcome parameter for the KSS was the score from 1 to 9.

All statistical tests were based on the 5% level of significance, except for the Bayesian methods used for the primary endpoint. Details of statistical methods and analyses were specified in the Statistical Analysis Plan (SAP) and body of the clinical study report.

The Safety Analysis Set was the group of subjects who received at least 1 dose of study drug and had at least 1 postdose safety assessment. The Full Analysis Set (FAS) was the group of randomized subjects who received at least 1 dose of study drug and had at least 1 postdose primary efficacy measurement. The PK Analysis Set was the group of randomized subjects who received at least 1 dose of compound A and had at least 1 quantifiable compound A concentration. The PD Analysis Set was the group of subjects who had sufficient PD data to derive at least 1 PD parameter. The PK/PD Analysis Set was the group of randomized subjects who received at least 1 dose of compound A or placebo, and had at least 1 quantifiable concentration of compound A concentration (active subjects), and at least 1 postdose PD assessment.

A difference from placebo of at least 6% in the change from baseline of mean SE at Day 1 and Day 2 was considered the minimum clinically significant difference (CSD).

Each dose was assessed for next-day residual sleepiness using the KSS. A mean difference of change from baseline in KSS at 1 hour after waketime on Day 2 and Day 3 of less than 4 units was incorporated into the utility function. A dose of compound A was considered to have an acceptable KSS at Day 15 and Day 16 if the mean difference of change from baseline in KSS at 1 hour after waketime on Day 15 and Day 16 at this dose relative to placebo was less than 4 units. Operationally, acceptable KSS for Day 15 and Day 16 was defined as the lower boundary of a 90% confidence interval (CI) being less than 4 units (of the mean difference of change from baseline in KSS at 1 hour after waketime at this dose relative to placebo).

Utility Function: The utility at a dose was a function of both SE and KSS, constructed by specifying the 1-dimensional component for each endpoint and then combining them multiplicatively. Sufficient utility was defined as a Pr(Utility>1).

Maximum Utility Dose (dUmax): The dose that produced the maximum utility score, ie, the best combination of efficacy and residual sleepiness as judged by the utility above.

The PK/PD Analysis Set was used to evaluate relationships between compound A concentrations and selected PD parameters. The relationships between exposure to compound A and selected PD endpoints (eg. KSS, DSST, RTI) were explored graphically and could be followed by population PK/PD modeling. The relationship between plasma concentrations of compound A at predose (trough), and within 1 hour after morning waketime, and selected PD parameters, was analyzed using Nonmem version 7.2 or later.

Results

The summary statistics for change from baseline in SE are presented in Table 5. All compound All doses were statistically significant against placebo for the change from baseline of Mean of Days 1/2. Doses compound A 2.5 mg and above were statistically significant against placebo for the change from baseline of Mean of Days 14/15. There was no statistical evidence of an increase or decrease in SE for the change from baseline of the mean of Days 1/2 compared to Days 14/15, indicating no loss of treatment effect.

In Table 5, "Baseline" was defined as the mean of the screening PSG 1 and 2, within −9 to −3 days of randomization. "LS Means Diff" refers to the differences between LS Means of Placebo and each compound A dose, "95% CI" means to 95% CI of LS Means Diff. "p-value" was analyzed using analysis of covariance (ANCOVA) with baseline as a covariate.

TABLE 5

Summary Statistics for Change from Baseline in SE (%)

| | | Compound A | | | | | |
|---|---|---|---|---|---|---|---|
| | Placebo | 1 mg | 2.5 mg | 5 mg | 10 mg | 15 mg | 25 mg |
| Baseline | | | | | | | |
| N | 56 | 32 | 27 | 38 | 32 | 56 | 50 |
| Mean | 66.5 | 61.7 | 61.3 | 63.1 | 65.1 | 65.1 | 66.6 |
| SD | 9.25 | 12.30 | 14.7 | 12.48 | 11.75 | 12.19 | 10.94 |
| (A) Change from Baseline of Mean of Days 1 & 2 | | | | | | | |
| N | 56 | 32 | 27 | 38 | 32 | 56 | 50 |
| Mean | 12.6 | 21.1 | 21.3 | 21.2 | 21.9 | 23.8 | 22.7 |

TABLE 5-continued

Summary Statistics for Change from Baseline in SE (%)

| | | | Compound A | | | | |
|---|---|---|---|---|---|---|---|
| | Placebo | 1 mg | 2.5 mg | 5 mg | 10 mg | 15 mg | 25 mg |
| SD | 12.18 | 11.21 | 14.1 | 13.20 | 11.92 | 12.22 | 10.98 |
| LS Means Diff | | 4.57 | 4.44 | 5.74 | 8.09 | 10.06 | 10.13 |
| 95% CI | | 1.19, 7.94 | 0.86, 8.01 | 2.54, 8.93 | 4.73, 11.45 | 7.20, 12.93 | 7.18, 13.08 |
| p-value | | 0.0083 | 0.0151 | 0.0005 | <0.0001 | <0.0001 | <0.0001 |
| (B) Change from Baseline of Mean of Days 14 & 15 | | | | | | | |
| N | 52 | 31 | 27 | 37 | 31 | 54 | 46 |
| Mean | 12.3 | 17.5 | 20.7 | 21.0 | 21.7 | 21.2 | 21.4 |
| SD | 10.53 | 13.62 | 14.66 | 15.43 | 13.37 | 12.92 | 9.96 |
| LS Means Diff | | 0.34 | 3.94 | 5.76 | 7.78 | 7.89 | 8.87 |
| 95% CI | | −3.22, 3.90 | 0.22, 7.66 | 2.40, 9.12 | 4.24, 11.32 | 4.86, 10.92 | 5.72, 12.02 |
| p-value | | 0.8505 | 0.038 | 0.0008 | <0.0001 | <0.0001 | <0.0001 |
| (B)-(A) (Potential Habituation Effect) | | | | | | | |
| N | 52 | 31 | 27 | 37 | 31 | 54 | 46 |
| Mean | −0.1 | −4.0 | −0.5 | 0.1 | −0.7 | −2.3 | −2.1 |
| SD | 7.19 | 8.19 | 10.51 | 6.89 | 6.88 | 6.60 | 5.39 |
| LS Means Diff | | −3.3 | 0.3 | 1.0 | 0.3 | −1.3 | −1.1 |
| 95% CI | | −6.5, 0.0 | −3.1, 3.7 | −2.1, 4.0 | −3.0, 3.5 | −4.1, 1.4 | −4.0, 1.8 |
| p-value | | 0.0506 | 0.8790 | 0.5441 | 0.8651 | 0.3438 | 0.4493 |

The summary statistics for change from baseline in KSS at 1 hour post waketime are presented in Table 6. The LS mean differences between placebo and compound A 1 mg to 15 mg were not statistically significant on the Mean of Days 2/3. Only the LS mean difference between placebo and compound A 25 mg was statistically significant on the Mean of Days 2/3 (LS mean difference 0.47; P=0.0393), indicating that subjects rated themselves worse than placebo subjects. This result was similar for the mean of Days 15/16 at 1 hour post waketime. The 2 hour post waketime assessments for both the mean of Days 2/3 showed statistical significance for compound A 15 mg and 25 mg, while the mean of Days 15/16 was statistically significant for compound A 25 mg. No statistically significant differences were seen at the 15 min post waketime timepoints.

In Table 6, "Baseline" was defined as the time-matched value on Day 1. "LS Means Diff" refers to the differences between LS Means of Placebo and each compound A dose, "95% CI" means to 95% CI of LS Means Diff. "p-value" was analyzed using analysis of covariance (ANCOVA) with baseline as a covanate.

Summary Statistics for Change from Baseline in KSS, 1 hour post waketime

| | | | Compound A | | | | |
|---|---|---|---|---|---|---|---|
| | Placebo | 1 mg | 2.5 mg | 5 mg | 10 mg | 15 mg | 25 mg |
| Baseline | | | | | | | |
| N | 55 | 32 | 27 | 38 | 32 | 56 | 50 |
| Mean | 4.0 | 4.0 | 4.0 | 4.3 | 3.8 | 4.1 | 3.7 |
| SD | 2.01 | 1.82 | 1.59 | 1.61 | 1.77 | 1.91 | 1.76 |
| Median | 4.0 | 4.0 | 4.0 | 4.0 | 3.5 | 4.0 | 3.0 |
| Min, Max | 1.0, 9.0 | 1.0, 8.0 | 1.0, 8.0 | 2.0, 8.0 | 1.0, 8.0 | 1.0, 8.0 | 1.0, 8.0 |
| (A) Change from Baseline of Mean of Days 2 & 3 | | | | | | | |
| N | 55 | 32 | 27 | 38 | 32 | 56 | 50 |
| Mean | −0.2 | −0.2 | −0.3 | −0.1 | 0.0 | 0.1 | 0.4 |
| SD | 1.27 | 0.97 | 1.00 | 1.54 | 1.51 | 1.59 | 1.36 |
| LS Means Diff | | 0.02 | −0.06 | 0.20 | 0.16 | 0.32 | 0.47 |
| 95% CI | | −0.49, 0.54 | −0.61, 0.48 | −0.29, 0.68 | −0.36, 0.67 | −0.11, 0.76 | 0.02, 0.93 |
| p-value | | 0.9290 | 0.8177 | 0.4304 | 0.5485 | 0.1471 | 0.0393 |
| (B) Change from Baseline of Mean of Days 15 & 16 | | | | | | | |
| N | 51 | 31 | 27 | 37 | 31 | 54 | 46 |
| Mean | −0.2 | 0.3 | −0.1 | 0.1 | −0.1 | 0.1 | 0.6 |
| SD | 1.43 | 1.22 | 1.12 | 1.39 | 1.57 | 1.72 | 1.51 |
| LS Means Diff | | 0.51 | 0.13 | 0.43 | 0.01 | 0.38 | 0.68 |
| 95% CI | | −0.03, 1.06 | −0.44, 0.70 | −0.09, 0.94 | −0.54, 0.55 | −0.08, 0.85 | 0.19, 1.17 |
| p-value | | 0.0651 | 0.6490 | 0.1059 | 0.9818 | 0.1071 | 0.0063 |

The summary statistics for change from baseline in LPS are presented in Table 7. As a result of a non-normal distribution, the data were log-transformed and analyzed using ANCOVA as pre-specified. The geometric mean ratio between placebo and compound A 1 mg was not statistically significant for the change from baseline of Mean of Days 1/2. The geometric mean ratios between placebo and all other active compound A showed evidence of statistical significance for the change from baseline of Mean of Days 1/2. Similar results were shown for the change from baseline of Mean of Days 14/15. Compound A 10 mg showed a statistical difference of change from baseline of the mean of Days 1/2 compared to Days 14/15, showing further improvement in LPS over time. On all other doses except compound A 10 mg, there was no other statistical evidence of an increase or decrease in LPS for the change from baseline of the mean of Days 1/2 compared to Days 14/15.

In Table 7, "Baseline" was defined as the mean of the screening PSG 1 and 2, within −9 to −3 days of randomization. "p-value" was analyzed using analysis of covariance (ANCOVA) with baseline as a covariate.

TABLE 7

Summary Statistics for Change from Baseline in LPS (mm)

| | Placebo | Compound A | | | | | |
|---|---|---|---|---|---|---|---|
| | | 1 mg | 2.5 mg | 5 mg | 10 mg | 15 mg | 25 mg |
| Baseline | | | | | | | |
| N | 56 | 32 | 27 | 38 | 32 | 56 | 50 |
| Mean | 58.8 | 69.9 | 73.0 | 70.4 | 67.9 | 72.5 | 64.3 |
| SD | 30.58 | 39.09 | 50.94 | 42.66 | 52.43 | 36.12 | 45.91 |
| Median | 55.8 | 68.60 | 68.5 | 61.4 | 52.3 | 68.9 | 52.1 |
| Min, Max | 7.3, 150.3 | 17.0, 160.8 | 3.3, 187.8 | 5.8, 164.3 | 11.3, 218.0 | 5.5, 188.3 | 2.8, 217.3 |
| (A) Change from Baseline of Mean of Days 1 & 2 | | | | | | | |
| N | 56 | 32 | 27 | 38 | 32 | 56 | 50 |
| Mean | −22.9 | −42.9 | −52.7 | −47.7 | −46.8 | −51.6 | −50.2 |
| SD | 44.46 | 41.86 | 50.15 | 39.39 | 46.11 | 36.73 | 43.14 |
| Median | −29.9 | −42.0 | −47.8 | −37.4 | −26.5 | −49.1 | −42.6 |
| Min, Max | −126.3, 174.8 | −136.0, 71.0 | −173.3, 18.3 | −140.5, 13.3 | −200.5, 3.0 | −176.0, 26.8 | −199.0, 18.8 |
| Geometric Mean Ratio (compound A/placebo) | | 0.77 | 0.55 | 0.60 | 0.54 | 0.52 | 0.39 |
| 95% CI | | 0.54, 1.09 | 0.38, 0.80 | 0.43, 0.83 | 0.38, 0.76 | 0.38, 0.70 | 0.29, 0.54 |
| p-value | | 0.1407 | 0.0018 | 0.0025 | 0.0006 | <0.0001 | <0.0001 |
| (B) Change from Baseline of Mean of Days 14 & 15 | | | | | | | |
| N | 52 | 31 | 27 | 37 | 31 | 54 | 46 |
| Mean | −22.4 | −41.2 | −54.2 | −51.7 | −56.1 | −51.6 | −50.8 |
| SD | 29.04 | 34.62 | 44.92 | 41.99 | 45.55 | 36.73 | 40.16 |
| Median | −23.9 | −34.3 | −48.5 | −47.3 | −39.5 | −49.1 | −41.6 |
| Min, Max | −79.0, 75.3 | −107.0, 27.8 | −165.0, −1.0 | −130.8, 28.5 | −178.5, 2.3 | −176.0, 26.8 | −200.0, 1.3 |
| Geometric Mean Ratio (compound A /placebo) | | 0.73 | 0.49 | 0.47 | 0.32 | 0.41 | 0.34 |
| 95% CI | | 0.49, 1.08 | 0.33, 0.75 | 0.32, 0.69 | 0.21, 0.47 | 0.29, 0.57 | 0.24, 0.48 |
| p-value | | 0.1158 | 0.001 | 0.0001 | <0.0001 | <0.0001 | <0.0001 |
| (B)-(A) (Potential Habituation Effect) | | | | | | | |
| N | 52 | 31 | 27 | 37 | 31 | 54 | 46 |
| Mean | 0.57 | 2.7 | −1.5 | −4.6 | −7.9 | −1.1 | 1.4 |
| SD | 40.85 | 24.33 | 22.12 | 22.34 | 17.41 | 24.57 | 12.05 |
| Median | 3.6 | 4.0 | −0.8 | −3.8 | −5.5 | −3.60 | −0.5 |
| Min, Max | −234.0, 66.8 | −43.3, 68.0 | −41.3, 62.5 | −90.0, 38.8 | −75.8, 22.0 | −49.5, 74.8 | −32.0, 35.5 |
| Geometric Mean Ratio (compound A/placebo) | | 0.93 | 0.90 | 0.77 | 0.60 | 0.76 | 0.89 |
| 95% CI | | 0.60, 1.44 | 0.57, 1.41 | 0.51, 1.17 | 0.39, 0.93 | 0.52, 1.10 | 0.60, 1.31 |
| p-value | | 0.7491 | 0.6354 | 0.2245 | 0.0216 | 0.1450 | 0.5493 |

The summary statistics for change from baseline in WASO are presented in Table 8. All compound A doses of 10 mg and above were statistically significant against placebo for the change from baseline of the mean of Days 1/2. Doses compound A 15 mg and above were statistically significant against placebo for the change from baseline of the mean of Days 14/15. There was no statistical evidence of an increase or decrease in WASO between the change from baseline of the mean of Days 1/2 compared to Days 14/15.

In Table 8, "Baseline" was defined as the mean of the screening PSG 1 and 2, within −9 to −3 days of randomization. "LS Means Diff" refers to the differences between LS Means of Placebo and each compound A dose, "95% CI" means to 95% CI of LS Means Diff. "p-value" was analyzed using analysis of covariance (ANCOVA) with baseline as a covariate.

tote, suggesting that there was no apparent additional benefit of higher compound A concentrations with regard to sleep onset. When modeled, WASO data were best described by log-linear relationships with the maximum observed concentration (Cmax). The exposure-response relationship for WASO showed a log-linear relationship with Cmax, such that higher concentrations of compound A at Cmax were associated with larger decreases in WASO. PK/PD analyses for next-day residual sleepiness assessments (KSS, DSST, and RTI) did not show any apparent relationship with time-matched compound A plasma concentrations. However, subjects whose compound A plasma concentrations were greater than 20 ng/mL at 1 hour after waking had slightly greater increases on the KSS and a higher incidence

TABLE 8

Summary Statistics for Change from Baseline in WASO (min)

| | Placebo | Compound A | | | | | |
|---|---|---|---|---|---|---|---|
| | | 1 mg | 2.5 mg | 5 mg | 10 mg | 15 mg | 25 mg |
| Baseline | | | | | | | |
| N | 56 | 32 | 27 | 38 | 32 | 56 | 50 |
| Mean | 108.9 | 121.2 | 119.8 | 113.7 | 103.5 | 103.3 | 103.0 |
| SD | 37.52 | 49.59 | 51.18 | 47.96 | 34.35 | 42.90 | 42.55 |
| (A) Change from Baseline of Mean of Days 1 & 2 | | | | | | | |
| N | 56 | 32 | 27 | 38 | 32 | 56 | 50 |
| Mean | −40.8 | −60.9 | −51.1 | −55.6 | −56.7 | −66.1 | −62.3 |
| SD | 46.18 | 36.69 | 46.37 | 52.28 | 35.45 | 44.25 | 41.18 |
| LS Means Diff | | −11.1 | −2.3 | −11.3 | −19.8 | −29.3 | −25.8 |
| 95% CI | | −24.5, 2.3 | −16.5, 11.9 | −23.9, 1.4 | −33.2, −6.4 | −40.8, −17.9 | −37.6, −14.1 |
| p-value | | 0.1050 | 0.7501 | 0.0818 | 0.0038 | <0.0001 | <0.0001 |
| (B) Change from Baseline of Mean of Days 14 & 15 | | | | | | | |
| N | 52 | 31 | 27 | 37 | 31 | 54 | 46 |
| Mean | −38.2 | −43.6 | −48.9 | −52.2 | −48.5 | −53.4 | −53.9 |
| SD | 45.35 | 54.27 | 55.86 | 59.22 | 40.17 | 46.97 | 42.51 |
| LS Means Diff | | 5.7 | −2.3 | −10.7 | −14.7 | −20.8 | −21.5 |
| 95% CI | | −9.6, 21.0 | −18.3, 13.6 | −25.1, 3.8 | −30.0, 0.5 | −33.9, −7.7 | −35.1, −7.9 |
| p-value | | 0.4642 | 0.7754 | 0.1461 | 0.0581 | 0.0019 | 0.0020 |
| (B)-(A) (Potential Habituation Effect) | | | | | | | |
| N | 52 | 31 | 27 | 37 | 31 | 54 | 46 |
| Mean | 6.0 | 18.0 | 2.2 | 2.7 | 9.3 | 11.8 | 9.3 |
| SD | 31.42 | 34.30 | 44.05 | 29.73 | 25.89 | 26.19 | 23.12 |
| LS Means Diff | | 13.2 | −2.9 | −2.9 | 2.8 | 5.2 | 2.7 |
| 95% CI | | −0.3, 26.7 | −17.0, 11.2 | −15.7, 9.8 | −10.6, 16.3 | −6.4, 16.7 | −9.3, 14.7 |
| p-value | | 0.0547 | 0.6852 | 0.6498 | 0.6796 | 0.3792 | 0.6635 |

The PK of compound A was best described by a 2-compartment model with elimination from the central compartment. Apparent clearance of compound A was independent of dose and time, indicating linearity in PK. Measures of the PD effects of compound A included KSS, RTI, DSST, the WFB (RTI, Rapid Visual Processing [RVP], and Spatial Span [SSP]), POMS, melatonin levels, and the DLMO. Due to high variability and non-normal distribution in change from baseline of LPS, it was not possible to reliably model the concentration-response relationship between compound A PK parameters and LPS. Nonetheless, higher plasma concentrations of compound A were associated with larger decreases in LPS, up to approximately 10 ng/mL. This finding was consistent with the efficacy results, where LPS was decreased at doses of 2.5 mg and higher. Above this concentration, the relationship appeared to reach an asympof AEs of somnolence. This concentration is predicted to be achieved by most subjects receiving doses greater than 10 mg.

Example 5 (Formulation)

Capsules used for Example 1, 2, and 3 consist of size 2 hypromellose capsules containing 1 mg, 2.5 mg, 10 mg, or 50 mg each of compound A drug substance. Compound A 25 mg capsules which consist of size 2 hypromellose capsules containing 25 mg compound A drug substance are also prepared only for the dissolution evaluation. The placebo consists of size 2 hypromellose capsules containing 10 mg of microcrystalline cellulose.

The components and compositions of tablets used for Examples 3 and 4 are shown in Table 9

TABLE 9

Components and Compositions of Compound A Tablets

| Component | 1 mg | 2.5 mg | Strength 5 mg | 10 mg | 25 mg |
|---|---|---|---|---|---|
| Core tablet (Internal phase) | | | | | |
| compound A | 1.0 | 2.5 | 5.0 | 10.0 | 25.0 |
| Lactose monohydrate | 97.88 | 96.38 | 93.88 | 88.88 | 222.2 |
| Low-substituted hydroxypropyl cellulose | 10.8 | 10.8 | 10.8 | 10.8 | 27.0 |
| Hydroxypropyl cellulose | 3.6 | 3.6 | 3.6 | 3.6 | 9.0 |
| (External phase) | | | | | |
| Low-substituted hydroxypropyl cellulose | 6.0 | 6.0 | 6.0 | 6.0 | 15.0 |
| Magnesium stearate | 0.72 | 0.72 | 0.72 | 0.72 | 1.8 |
| Film-coated tablet | | | | | |
| Opadry RED | 9.0 | 9.0 | 9.0 | 9.0 | 15.0 |
| Total Weight (mg) | 129 | 129 | 129 | 129 | 315 |

Conventional wet granulation method was used for the manufacturing for compound A film-coated tablets. The compound A film-coated tablets were manufactured through mixing, wet-granulation, drying, sizing, lubrication, tableting and film-coating process. Compound A, lactose monohydrate and low-substituted hydroxypropyl cellulose were mixed using mixer. The mixture was wet-granulated using mixer with gradually adding appropriate amount of the aqueous solution of hydroxypropyl cellulose. The wet granules were dried using a dryer. The dried granules are passed through a 1.0 mm screen using a screening mill. Low-substituted hydroxypropyl cellulose and magnesium stearate are weighed depending on the yield of granules. The granules, low-substituted hydroxypropyl cellulose and magnesium stearate are lubricated together in a mixer. The lubricated granules equivalent to one tablet were compressed into bi-convex tablets using a tablet press. The core tablets were coated using a coating machine with spraying the aqueous suspension of Opadry RED.

Test Example

Figure 2:
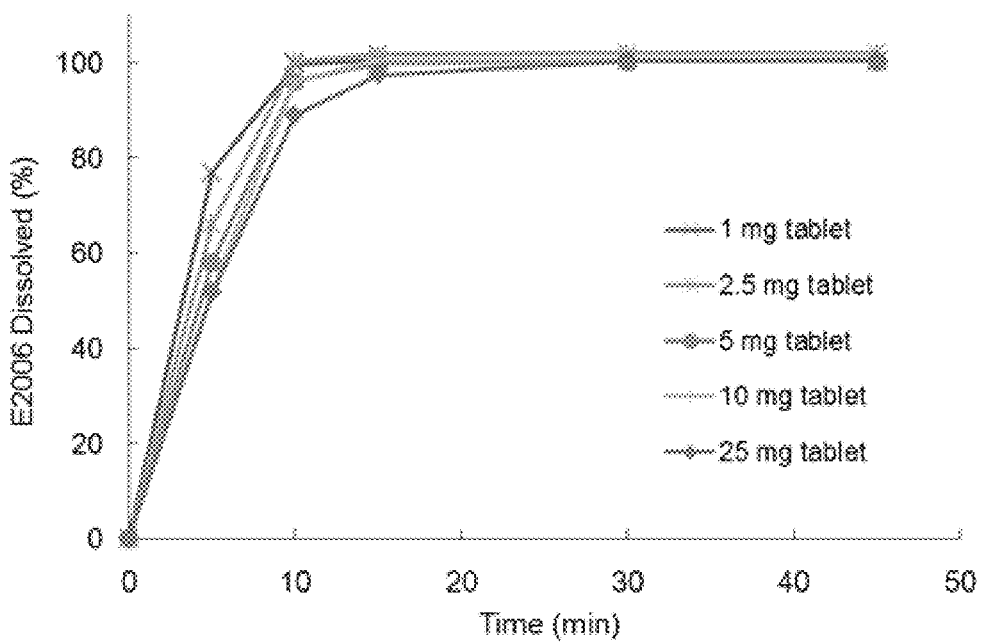
FIG. 2 shows Dissolution Profiles of compound A 1 mg, 2.5 mg, 5 mg, 10 mg and 25 mg Tablets
Figure 3:
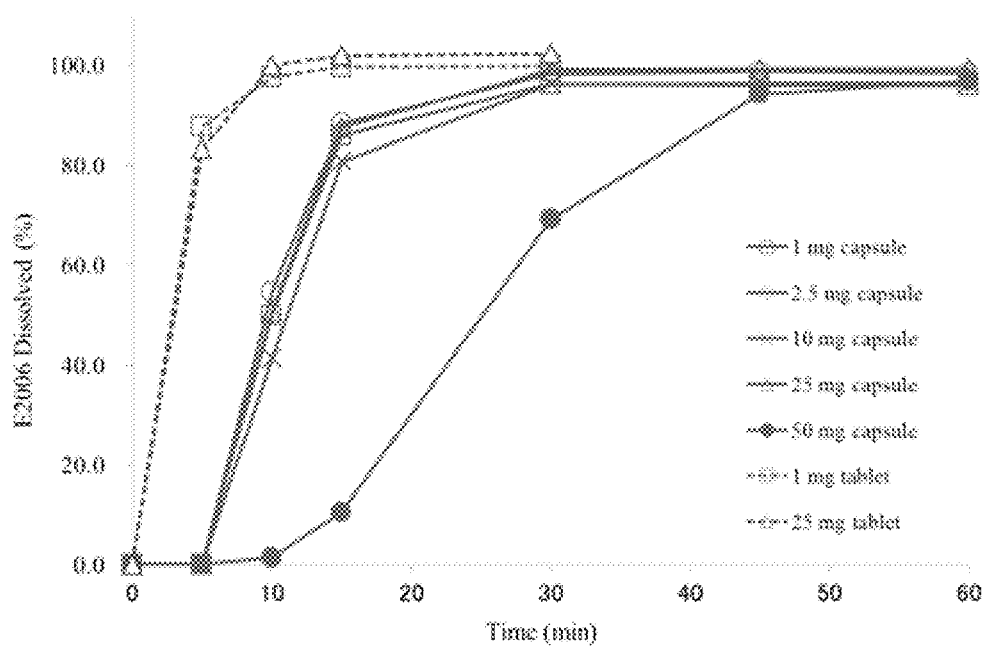
FIG. 3 shows Comparative Dissolution Profiles between Compound A Capsules and Tablets Obtained in Condition I

The dissolution test for the compound A capsules and tablets prepared in the Example 5 was executed using Apparatus 2 (paddle apparatus) according to JP 6.10, USP <711>, and Ph.Eur. 2.9.3. The capsules and tablets were tested in 900 mL of 0.1 mol/L hydrochloric acid containing 0.5% polysorbate 80 at the paddle rotation speed of 75 rpm (Condition I). In addition, the tablets were tested in 900 mL of 0.1 mol/L hydrochloric acid at the paddle rotation speed of 50 rpm (Condition II). A helical wire sinker was used in the tests for capsules. Aliquots of media were withdrawn through a filter (pore size: 0.45 μm) at the prescribed time point to make sample solutions. The standard solutions were prepared to have compound A concentrations corresponding to those of the sample solutions at nominal concentration level. The amount of compound A released was determined chromatographically compared to the standard solution. The dissolution conditions and HPLC conditions are provided in Table 10. Testing was carried out on 6 capsules/tablets and their average value was indicated in each case. Dissolution profiles of compound A 1 mg and 50 mg capsules obtained in Condition I are presented in FIG. 1 and Table 11. Dissolution profiles of compound A 1 mg, 2.5 mg, 5 mg, 10 mg and 25 mg tablets obtained in Condition II are presented in FIG. 2 and Table 12. Comparative dissolution profiles between compound A capsules and tablets obtained in Condition I are presented in FIG. 3 and Table 13. The difference between capsules and tablets was observed in the dissolution profiles, which was caused by the lag time for the disintegration of capsules.

TABLE 10

Dissolution Conditions and HPLC Conditions

| Parameter | Condition I | Condition II |
|---|---|---|
| Dissolution Conditions | | |
| Apparatus | Apparatus 2 (paddle apparatus) in accordance with JP 6.10, USP <711>, and Ph. Eur. 2.9.3 | |
| Paddle rotation speed | 75 rpm | 50 rpm |
| Dissolution medium | 0.1 mol/L hydrochloric acid containing 0.5% polysorbate 80 | 0.1 mol/L hydrochloric acid |
| Medium volume | 900 mL | |
| Medium temperature | 37° C. | |
| Sinker | Compound A capsules: helical wire sinkers Compound A tablets: N/A | |
| Sampling time | Compound A capsules: 5, 10, 15, 30, 45 and 60 minutes Compound A tablets: "5, 10, 15, and 30 minutes" or "5, 10, 15, 30, and 45 minutes" | |
| HPLC Conditions | | |
| Detection Wavelength | 283 nm | |
| Column | 4.6-mm × 7.5-cm column that contains 3.5-μm packing L1 (USP) | 4.6-mm × 7.5-cm column that contains 3-μm packing L1 (USP) |
| Column temperature | A constant temperature of about 40° C. | |
| Mobile phase | A: Water/70% perchloric acid (1000:1, v/v) B: Acetonitrile/70% perchloric acid (1000:1, v/v) Isocratic flow: A = 60% B = 40% | Water/acetonitrile/70% perchloric acid (550:450:1, v/v/v) |
| Flow rate | 1.0 mL/min | 1.2 mL/min |
| Injection volume | 10 μL | 50 μL |
| Sample cooler temperature | 25° C. | |
| Measurement time | 5 minutes after injection | |

TABLE 11

Dissolution Rates of Compound A 1 mg and 50 mg Capsules Obtained in Condition I

| Samples | Dissolution rate (%) | | | | | |
|---|---|---|---|---|---|---|
| | 5 min | 10 min | 15 min | 30 min | 45 min | 60 min |
| Compound A 1 mg capsules | 0.0 | 50.0 | 86.0 | 96.4 | 96.0 | 95.9 |
| Compound A 50 mg capsules | 0.0 | 1.4 | 10.6 | 69.2 | 94.3 | 96.9 |

TABLE 12

Dissolution Rates of Compound A 1 mg, 2.5 mg, 5 mg, 10 mg, and 25 mg Tablets Obtained in Condition II

| Samples | Dissolution rate (%) | | | | | |
|---|---|---|---|---|---|---|
| | 5 min | 10 min | 15 min | 30 min | 45 min | 60 min |
| Compound A 1 mg tablets | 77.0 | 99.7 | 100.5 | 100.6 | 100.4 | |
| Compound A 2.5 mg tablets | 66.1 | 100.2 | 101.7 | 101.9 | 102.0 | |
| Compound A 5 mg tablets | 58.0 | 96.1 | 99.7 | 100.3 | 100.2 | |
| Compound A 10 mg tablets | 52.2 | 96.2 | 100.6 | 100.9 | 100.9 | |
| Compound A 25 mg tablets | 51.7 | 89.0 | 97.5 | 100.4 | 100.5 | |

TABLE 13

Dissolution Rates of Compound A Capsules and Tablets Obtained in Condition I

| Samples | Dissolution rate (%) | | | | | |
|---|---|---|---|---|---|---|
| | 5 min | 10 min | 15 min | 30 min | 45 min | 60 min |
| Compound A 1 mg capsules | 0.0 | 50.0 | 86.0 | 96.4 | 96.0 | 95.9 |
| Compound A 2.5 mg capsules | 0.0 | 54.6 | 88.5 | 98.4 | 98.8 | 98.5 |
| Compound A 10 mg capsules | 0.0 | 41.4 | 80.7 | 96.2 | 96.6 | 96.5 |
| Compound A 25 mg capsules | 0.1 | 50.7 | 87.7 | 99.0 | 99.2 | 99.3 |
| Compound A 50 mg capsules | 0.0 | 1.4 | 10.6 | 69.2 | 94.3 | 96.9 |
| Compound A 1 mg tablets | 87.7 | 97.7 | 99.7 | 99.9 | | |
| Compound A 25 mg tablets | 83.3 | 100.0 | 102.0 | 102.3 | | |

What is claimed is:

1. A dosage form comprising a therapeutically effective amount of compound A, wherein said therapeutically effective amount is a single daily dose ranging from about 2.5 mg to about 10 mg, wherein said dosage form provides a dissolution rate of 85% or more in a dissolution medium (0.1 mol/L hydrochloric acid containing 0.5% polysorbate 80, 900 mL, 37±0.5° C.) within 30 minutes from the onset of a dissolution study using Apparatus 2 (Paddle Apparatus, paddle speed; 75 rpm) according to the procedure for immediate-release dosage form in 6.10 Dissolution test of JP16 or <711>Dissolution of USP37, wherein said compound A is (1R,2S)-2-(((2,4-dimethylpyrimidin-5-yl)oxy) methyl)-2-(3-fluorophenyl)-N-(5-fluoropyridine-2-yl)cyclopropanecarboxamide represented by the following formula:

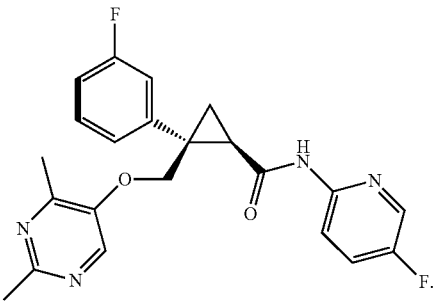

2. The dosage form of claim 1, wherein said dosage form provides a dissolution rate of 85% or more in a dissolution medium (0.1 mol/L hydrochloric acid, 900 mL, 37±0.5° C.) within 15 minutes from the onset of a dissolution study using Apparatus 2 (Paddle Apparatus, paddle speed; 50 rpm) according to the procedure for immediate-release dosage form in 6.10 Dissolution test of JP16 or <711>Dissolution of USP37.

3. The dosage form of claim 1, wherein said dosage form comprises lactose as a pharmaceutically acceptable excipient.

4. The dosage form of claim 1, wherein said dosage form comprises low-substituted hydroxypropyl cellulose as a pharmaceutically acceptable excipient.

5. The dosage form of claim 1, wherein said dosage form comprises lactose and low-substituted hydroxypropyl cellulose as pharmaceutically acceptable excipients.

* * * * *